US011185850B2

(12) United States Patent
Khokhar et al.

(10) Patent No.: US 11,185,850 B2
(45) Date of Patent: Nov. 30, 2021

(54) DUAL FUNCTIONAL COMPOSITE CATALYST FOR OLEFIN METATHESIS AND CRACKING

(71) Applicant: Saudi Arabian Oil Company, Dhahran (SA)

(72) Inventors: Munir D. Khokhar, Al-Khobar (SA); Zahra Almisbaa, Qatif (SA); Sohel K. Shaikh, Dhahran (SA); Raed Abudawoud, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 4 days.

(21) Appl. No.: 16/700,197

(22) Filed: Dec. 2, 2019

(65) Prior Publication Data

US 2021/0162384 A1    Jun. 3, 2021

(51) Int. Cl.

| | | |
|---|---|---|
| *B01J 29/06* | (2006.01) | |
| *B01J 29/78* | (2006.01) | |
| *B01J 21/08* | (2006.01) | |
| *B01J 29/48* | (2006.01) | |
| *B01J 31/06* | (2006.01) | |
| *B01J 31/34* | (2006.01) | |
| *B01J 35/02* | (2006.01) | |
| *B01J 37/02* | (2006.01) | |
| *B01J 37/03* | (2006.01) | |
| *B01J 37/04* | (2006.01) | |
| *C07C 6/04* | (2006.01) | |
| *B01J 29/076* | (2006.01) | |
| *B01J 29/70* | (2006.01) | |
| *B01J 29/40* | (2006.01) | |
| *B01J 35/00* | (2006.01) | |
| *B01J 37/00* | (2006.01) | |
| *B01J 37/08* | (2006.01) | |

(52) U.S. Cl.
CPC .............. *B01J 29/78* (2013.01); *B01J 21/08* (2013.01); *B01J 29/061* (2013.01); *B01J 29/076* (2013.01); *B01J 29/40* (2013.01); *B01J 29/405* (2013.01); *B01J 29/48* (2013.01); *B01J 29/7049* (2013.01); *B01J 31/06* (2013.01); *B01J 31/34* (2013.01); *B01J 35/002* (2013.01); *B01J 35/0006* (2013.01); *B01J 35/0026* (2013.01); *B01J 35/023* (2013.01); *B01J 35/026* (2013.01); *B01J 37/0009* (2013.01); *B01J 37/0045* (2013.01); *B01J 37/0063* (2013.01); *B01J 37/0236* (2013.01); *B01J 37/038* (2013.01); *B01J 37/04* (2013.01); *B01J 37/08* (2013.01); *C07C 6/04* (2013.01); *B01J 2229/186* (2013.01); *C07C 2529/076* (2013.01); *C07C 2529/40* (2013.01); *C07C 2529/48* (2013.01); *C07C 2529/70* (2013.01); *C07C 2529/78* (2013.01)

(58) Field of Classification Search
CPC ........ B01J 29/061; B01J 29/076; B01J 29/40; B01J 29/405; B01J 29/48; B01J 29/78; B01J 29/7049; B01J 2229/18; B01J 2229/186; B01J 2229/20; B01J 2229/42; B01J 21/04; B01J 21/06; B01J 21/063; B01J 21/08; B01J 31/32; B01J 31/36; B01J 31/38; B01J 31/34; B01J 31/06; B01J 35/0006; B01J 35/002; B01J 35/0026; B01J 35/023; B01J 35/026; B01J 37/0009; B01J 37/0045; B01J 37/0063; B01J 37/0236; B01J 37/08; B01J 37/04; B01J 37/038; C07C 2529/40; C07C 2529/48; C07C 2529/70; C07C 2529/78; C07C 2529/076
USPC ...................... 502/60, 63, 64, 65, 69, 70, 71
See application file for complete search history.

(56) References Cited

U.S. PATENT DOCUMENTS

| | | |
|---|---|---|
| 3,702,886 A | 11/1972 | Argauer et al. |
| 3,956,474 A | 5/1976 | Ritsko |
| 4,198,319 A | 4/1980 | Alafandi et al. |
| 4,575,575 A | 3/1986 | Drake et al. |
| 5,026,936 A | 6/1991 | Leyshon et al. |
| 5,776,852 A | 7/1998 | Wu et al. |
| 6,111,157 A | 8/2000 | Hendriksen et al. |

(Continued)

FOREIGN PATENT DOCUMENTS

| | | |
|---|---|---|
| CN | 109382129 A | 2/2019 |
| EP | 0036707 B1 | 10/1985 |

(Continued)

OTHER PUBLICATIONS

International Search Report and Written Opinion dated Aug. 5, 2020 pertaining to International application No. PCT/US2020/031416 filed May 5, 2020, 13 pgs.

(Continued)

*Primary Examiner* — Elizabeth D Wood
(74) *Attorney, Agent, or Firm* — Dinsmore & Shohl LLP

(57) ABSTRACT

Composite catalysts includes zeolite particles at least partially embedded in a catalyst support material and at least one catalytically active compound deposited on the outer surfaces and pore surfaces of the catalyst support material, zeolite particles, or both. A method of making the composite catalysts may include preparing a catalyst precursor mixture that includes the zeolite, catalyst support material, triblock copolymer surfactant, and the catalytically active compound precursor and spray drying the catalyst precursor mixture. The composite catalysts may be used as a single catalyst for conducting olefin metathesis and cracking reactions. A method for producing propene may include contacting a butene-containing feed with the composite catalysts.

15 Claims, 4 Drawing Sheets

(56) References Cited

U.S. PATENT DOCUMENTS

| | | | |
|---|---|---|---|
| 6,162,350 | A | 12/2000 | Soled et al. |
| 6,420,619 | B1 | 7/2002 | Gartside et al. |
| 6,518,349 | B1 | 2/2003 | Felix et al. |
| 6,586,649 | B1 | 7/2003 | Botha et al. |
| 6,960,556 | B2 | 11/2005 | Gingerich |
| 7,084,087 | B2 | 8/2006 | Shan et al. |
| 7,648,939 | B2 | 1/2010 | Domokos et al. |
| 7,754,647 | B2 | 7/2010 | Schubert et al. |
| 7,960,308 | B2 | 6/2011 | Fukumoto |
| 8,153,851 | B2 | 4/2012 | Gartside et al. |
| 8,440,874 | B2 | 5/2013 | Ramachandran et al. |
| 9,234,060 | B2 | 1/2016 | Kao et al. |
| 9,260,355 | B2 | 2/2016 | Vermeiren et al. |
| 9,718,050 | B2 | 8/2017 | Bonduelle et al. |
| 10,329,225 | B2 | 6/2019 | Khokhar et al. |
| 2005/0124839 | A1 | 6/2005 | Gartside et al. |
| 2008/0004462 | A1 | 1/2008 | Peters et al. |
| 2011/0092757 | A1 | 4/2011 | Akagishi et al. |
| 2011/0196185 | A1 | 8/2011 | Krawczyk et al. |
| 2012/0283090 | A1 | 11/2012 | Popp et al. |
| 2014/0021096 | A1 | 1/2014 | Chaumonnot et al. |
| 2018/0155256 | A1* | 6/2018 | Al-Khattaf ............... C07C 6/04 |
| 2018/0326408 | A1* | 11/2018 | Al-Khattaf ............... B01J 23/30 |
| 2018/0327338 | A1* | 11/2018 | Shaikh ................ B01J 35/0006 |
| 2019/0118164 | A1* | 4/2019 | Alshafei ................ B01J 35/002 |
| 2019/0255519 | A1 | 8/2019 | Ostraat et al. |

FOREIGN PATENT DOCUMENTS

| | | |
|---|---|---|
| WO | 2006060354 A1 | 6/2006 |
| WO | 2006089957 A1 | 8/2006 |
| WO | 2017003821 A1 | 1/2017 |

OTHER PUBLICATIONS

Debecker et al. "Aerosol route to nanostructured $WO_3$—$SiO_2$—$Al_2O_3$ metathesis catalysts: Toward higher propene yield" Applied Catalysis A: General 470 (2014) 458-466, 9 pgs.

Debecker et al. "Aerosol processing: a wind of innovation in the field of advanced heterogeneous catalysts" In: Chemical Society Reviews, vol. 47, p. 4112-4155 (2018) http://hdl.handle.net/2078.1/198809—DOI: 10.1039/C7CS00697G, 48 pgs.

Xie et al. "An Overview of Recent Development in Composite Catalysts from Porous Materials for Various Reactions and Processes" Int. J. Mol. Sci. 2010, 11, 2152-2187; doi:10.3390/ijms11052152, 36 pgs.

Zhao et al. "Entrapped Single Tungstate Site in Zeolite for Cooperative Catalysis of Olefin Metathesis with Bronsted Acid Site" J. Am. Chem. Soc. 2018, 140, 6661-6667, 7 pgs.

International Search Report and Written Opinion for International Application No. PCT/US2018/056999 dated Jan. 11, 2019.

Maksasithorn et al. "Preperation of super-microporous $WO_3$—$SiO_2$ olefin metathesis catalysts by the aerosol-assisted sol-gel process", Microporous and Mesoporous Materials, 2015, pp. 125-133.

\* cited by examiner

DUAL FUNCTIONAL COMPOSITE CATALYST FOR OLEFIN METATHESIS AND CRACKING

TECHNICAL FIELD

The present disclosure is directed to hydrocarbon processing, in particular, to composite catalysts and methods of making composite catalysts for conducting olefin metathesis and cracking.

BACKGROUND

In recent years, there has been a dramatic increase in the demand for propene to feed the growing markets for polypropylene, propylene oxide, and acrylic acid. Currently, most of the propene produced worldwide (74 million tons/year) is a by-product from steam cracking units (57%), which primarily produce ethylene, or a by-product from Fluid Catalytic Cracking (FCC) units (30%), which primarily produce gasoline. These processes cannot respond adequately to a rapid increase in propene demand.

Production of propene from a butene-containing stream, such as a Raffinate stream or other butene-containing stream, can be accomplished through metathesis of the butene to propene and other compounds in combination with cracking, isomerization, or both. Some propene processes include metathesis, isomerization, and cracking in order to increase the overall yield and propene selectivity of the reaction system. Each of these types of reactions can require a different type of catalyst, such as a cracking catalyst for the cracking reaction, a metathesis catalyst for the metathesis reaction, and an isomerization catalyst for the isomerization reaction. In conventional reaction system for converting butene to propene, the separate catalysts may be isolated in separate catalyst zones, such as by charging each of the separate catalysts to a separate reactor or by charging the catalyst to a single reactor and separating each catalyst with inert spacers, such as quartz wool or silicon carbide. Segregating the catalysts into separate reactor vessels substantially increases the initial capital cost of the reaction system. Additionally, separating the catalysts with inert spacers creates dead volumes in the reactor, which may reduce the efficiency of the reactor.

To reduce costs and eliminate dead zones, a physical catalyst mixture of two or more separate solid particulate catalyst materials may be used. However, these physical catalyst mixtures of different solid catalyst materials may gradually segregate in the reactor over time due to settling that occurs with continuing use and handling. This segregation, or settling, effect can be increasingly drastic when, for example, the physical properties of the separate solid particulate catalyst materials are significantly different, relative to the other catalyst materials in the physical catalyst mixture. Thus, the effectiveness of the physical catalyst mixtures of solid catalyst particles may decrease over time as the separate catalysts segregate through settling.

SUMMARY

Accordingly, there is an ongoing need for multi-functional composite catalysts and methods of synthesizing the composite catalysts. The present disclosure is directed to multi-functional composite catalysts and methods of producing the composite catalysts. The composite catalysts of the present disclosure may include a plurality of composite catalyst particles and each of the composite catalyst particles may include a plurality of different catalytically active constituents. Each of the plurality of catalytically active constituents in the composite catalyst may provide a different catalytic functionality to the composite catalyst particles. Thus, the multi-functional composite catalyst may combine multiple catalytic functionalities into a single particle. In particular, the composite catalysts of the present disclosure may include zeolite particles at least partially or fully embedded in a catalyst support material and a catalytically active compound deposited on the surfaces of the catalyst support material, the zeolite particles, or both. The composite catalyst may have a uniform distribution of the catalytically active compound across the outer surfaces and pore surfaces of the catalyst support material, the zeolite particles, or both. Thus, the composite catalyst may have substantially uniform physical properties and may not experience the drawbacks associated with settling of physical catalyst mixtures. The multi-functional composite catalyst may enable a single particulate catalyst to be charged to a reactor to conduct a plurality of different chemical reactions, such as combinations of isomerization, metathesis, and cracking, for producing propene from 2-butene, for example.

According to embodiments of the present disclosure, a method of preparing a composite catalyst may include combining a catalyst support material, zeolite particles, a triblock copolymer surfactant, a catalytically active compound precursor, and a diluent to produce a catalyst precursor composition. The method may further include mixing the catalyst precursor composition to produce a catalyst precursor mixture in which the catalyst support material and the zeolite particles are suspended in the diluent and spray drying the catalyst precursor mixture. The spray drying may include atomizing the catalyst precursor mixture to produce a plurality of droplets and drying the plurality of droplets in a drying chamber. Drying may remove the diluent from each of the plurality of droplets to form agglomerates comprising the zeolite particles at least partially secured within the catalyst support material. Drying may also cause the catalytically active compound precursor to react to form a catalytically active compound deposited on outer surfaces and pore surfaces of the catalyst support material, the zeolite particles, or both.

According to embodiments of the present disclosure, a method for producing propene may include contacting a butene-containing feed with a composite catalyst at a reaction temperature. The contacting may cause at least a portion of the butene to undergo chemical reaction to produce a reaction effluent comprising at least propene. The composite catalyst may be prepared by a method that may include combining a catalyst support material, zeolite particles, a triblock copolymer surfactant, a catalytically active compound precursor, and a diluent to produce a catalyst precursor composition. The method of preparing the composite catalyst may further include mixing the catalyst precursor composition to produce a catalyst precursor mixture in which the catalyst support material and the zeolite particles are suspended in the diluent and spray drying the catalyst precursor mixture. The spray drying may include atomizing the catalyst precursor mixture to produce a plurality of droplets and drying the plurality of droplets in a drying chamber. Drying may remove the diluent from each of the plurality of droplets to form agglomerates comprising the zeolite particles at least partially secured within the catalyst support material. Drying may also cause the catalytically active compound precursor to react to form a catalytically active compound deposited on outer surfaces and pore surfaces of the catalyst support material, the zeolite particles, or both. The method for producing propene may further include separating at least a portion of the propene from the reactor effluent.

Additional features and advantages of the described embodiments will be set forth in the following detailed description and, in part, will be readily apparent to those skilled in the art from that detailed description or recognized by practicing the described embodiments, including the detailed description, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
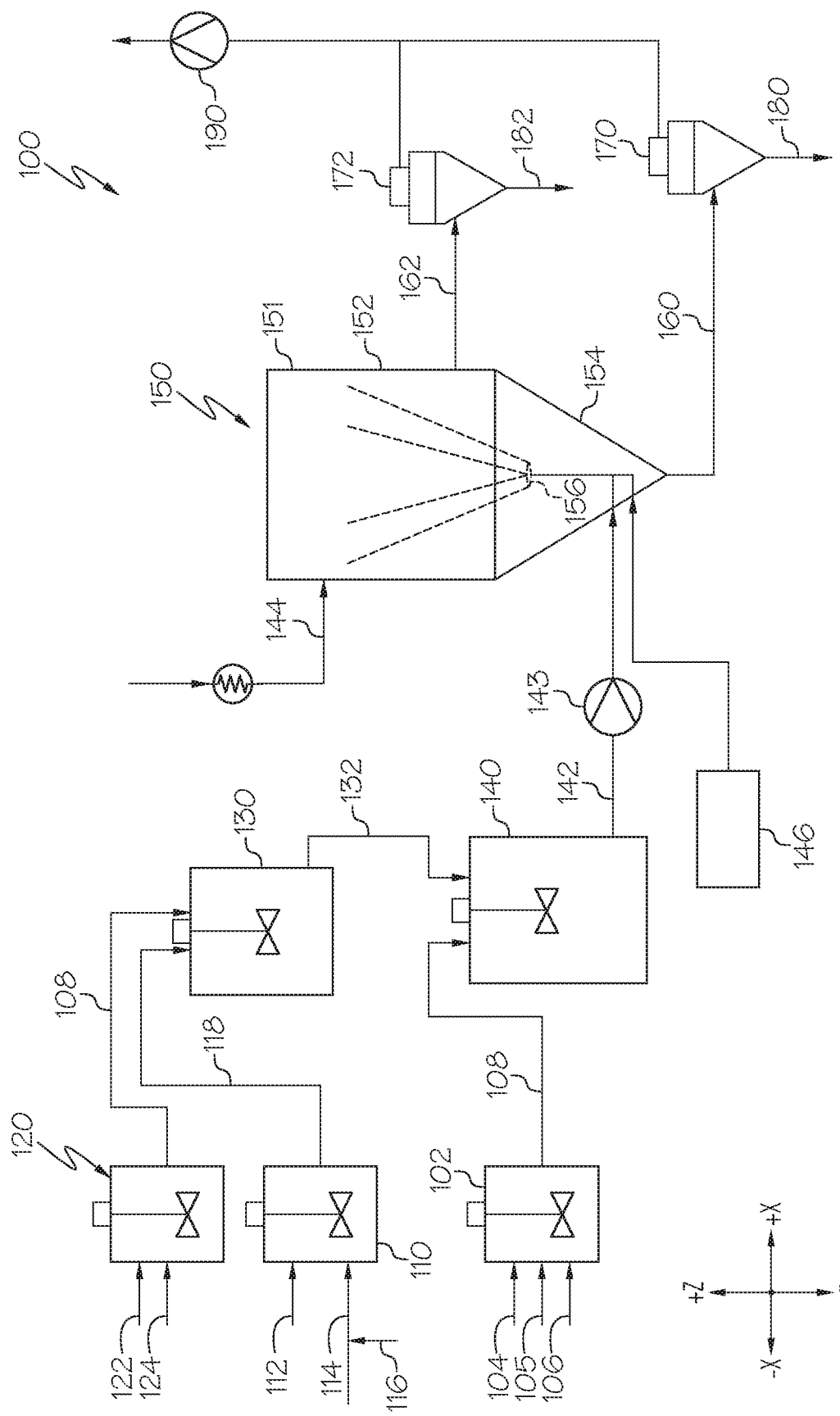
FIG. 1 schematically depicts a spray dryer system for preparing a composite catalyst, according to one or more embodiments shown and described in the present disclosure.
Figure 2:
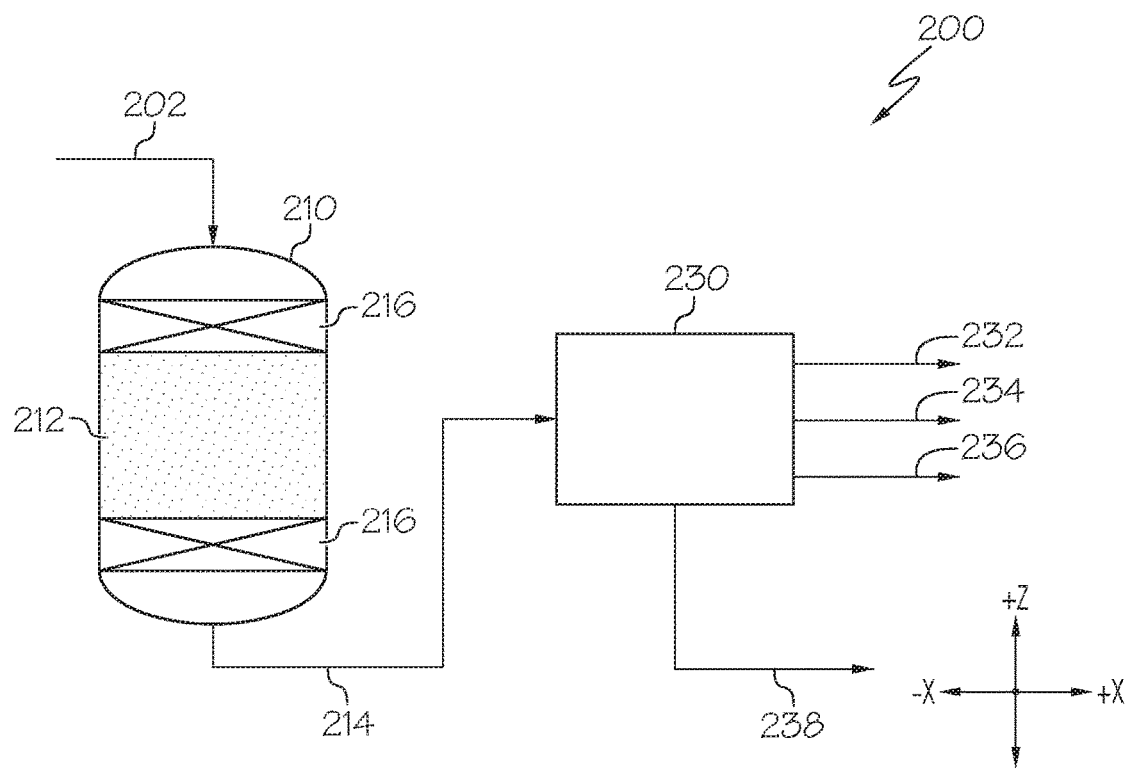
FIG. 2 schematically depicts a reactor system for conducting a metathesis reaction, according to one or more embodiments shown and described in the present disclosure.

For the purpose of describing the simplified schematic illustrations and descriptions of FIGS. 1 and 2 the numerous valves, temperature sensors, electronic controllers, and similar processing components that may be employed and well known to those of ordinary skill in the art of certain chemical processing operations may not be included. Further, accompanying components that are often included in typical chemical processing operations, carrier gas supply systems, pumps, vessel agitators, compressors, furnaces, or other subsystems may not be depicted. It should be understood that these components and subsystems are within the spirit and scope of the present embodiments disclosed. However, operational components, such as those described in the present disclosure, may be added to the embodiments described in this disclosure.

Arrows in the Figures refer to process streams. However, the arrows may equivalently refer to transfer lines which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system or a system inlet stream which enters the depicted system. Product streams may be further processed in accompanying systems or may be commercialized as end products.

Additionally, arrows in the Figures may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1 and 2. Mixing or combining may also include mixing by directly introducing both streams into a like system component, such as a vessel, reactor, separator, or other system component. For example, it should be understood that when two streams are depicted as being combined directly prior to entering a system component, the streams could equivalently be introduced into the system component and be mixed in the system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

The present disclosure is directed to multi-functional composite catalysts and methods of preparing the composite catalysts. In particular, the composite catalyst may include a catalyst support material, zeolite particles at least partially or fully embedded within the catalyst support material, and a catalytically active compound providing catalytically active sites at outer and pore surfaces of the catalyst support material, the zeolite particles, or both. The composite catalyst may be prepared through a spray drying process that includes combining a catalyst support material, zeolite particles, a triblock copolymer surfactant, at least one catalytically active compound precursor, and a diluent to produce a catalyst precursor composition. The method may further include mixing the catalyst precursor composition to produce a catalyst precursor mixture in which the catalyst support material and the zeolite particles are suspended in the diluent. The method may further include spray drying the catalyst precursor mixture, which may include atomizing the catalyst precursor mixture to produce a plurality of droplets and drying the droplets in a drying chamber. The drying may remove the diluent from the droplets to form agglomerates comprising the zeolite particles at least partially secured within the catalyst support material and may cause the catalytically active compound precursor to react to form the catalytically active compound deposited on the outer surface and pore surfaces of the catalyst support material, the zeolite particles, or both.

The composite catalyst may provide a multi-functional catalyst having multiple distinct catalytic species, each catalytic species may be capable of catalyzing a different reaction independent of the other catalytic species in the composite catalyst. For example, the composite catalyst may be useful for converting 2-butene to propene through metathesis and may include the zeolite particles and a metal oxide, such as but not limited to tungsten oxide, as the catalytically active compound. The metal oxide may be catalytically active to cross-metathesize 1-butene and 2-butene to produce propene, pentene, and optionally other C6+ olefins. The zeolite particles may catalyze cracking of pentene or other C6+ olefins into propene and other smaller olefins during the metathesis reaction.

The composite catalyst may enable a reaction system to perform multiple catalytic reactions, such as metathesis and cracking, without requiring handling and management of multiple catalyst materials. Further, use of the composite catalyst may eliminate or reduce the need to install spacer materials in a reactor to separate catalyst beds having different catalysts. This may eliminate or reduce dead zones from a reactor. Dead zones are zones in which no reaction takes place, such as due to the presence of inert spacing materials. In some conventional reaction systems, a blend or physical mixture of two separate dry particulate catalysts may be prepared and charged to the reactor. Although a dry blend of two particulate catalysts may initially provide a multi-functional catalytic environment within a reactor system, one of the particulate catalysts may eventually settle to the bottom of the reactor under the force of gravity, which may create a separation of the two blended catalysts into separate zones in the reactor. Such separation may lead to undesirable shifts in the efficiency of the reaction system as the separate catalysts settle and develop zones within the catalyst bed with varied concentrations of the two blended catalysts. The composite catalyst described in this disclosure may reduce or eliminate the problems associated with a blended catalyst settling out in a reaction system over time.

As used in this disclosure, a "catalyst" may refer to a solid particulate that includes at least one catalytically active compound that increases the rate of a specific chemical reaction, increases the selective production of certain products in a reaction, or both.

As used through the present disclosure, the term "mesoporous" may refer to a material having an average pore size of from 2 nanometers (nm) to 50 nm.

As used in this disclosure, a "catalytically active compound" may refer to a substance that increases the rate of a specific chemical reaction, increases the selective production of certain products in a reaction, or both. Catalytically active compounds and the catalysts made with the catalytically active compounds described in this disclosure may be utilized to promote various reactions, such as, but not limited to, isomerization, metathesis, cracking, hydrogenation, demetalization, desulfurization, denitrogenation, other reactions, or combinations of these.

As used in this disclosure, "catalytic activity" may refer to a degree to which a catalyst or a catalytically active compound increases the reaction rate of a reaction. Greater catalytic activity of a catalyst increases the reaction rate of a reaction compared to a catalyst having a lesser catalytic activity.

As used in this disclosure, a "stable" mixture refers to a solids-liquid mixture in which the liquid portion includes dissolved solids that do not precipitate out of the liquid portion. The dissolved solids in the liquid portion of a stable mixture, for example, will not precipitate out during later processing steps of the method disclosed herein.

As used throughout the present disclosure, the term "butene" or "butenes" may refer to compositions comprising one or more than one of 1-butene, trans-2-butene, cis-2-butene, isobutene, or mixtures of these isomers. As used throughout the present disclosure, the term "normal butenes" may refer to compositions comprising one or more than one of 1-butene, trans-2-butene, cis-2-butene, or mixtures of these isomers, and does not include isobutene. As used throughout the present disclosure, the term "2-butene" may refer to trans-2-butene, cis-2-butene, or a mixture of these two isomers.

As previously discussed, the composite catalyst may be a spray dried catalyst that includes zeolite particles at least partially or fully surrounded by or embedded within agglomerates formed of the catalyst support material and at least one catalytically active compound deposited on surfaces of the catalyst support material, the zeolite particles, or both. The agglomerates of the catalyst support material and zeolite particles may be formed by agglomeration of the catalyst support material during spray drying. The catalyst support material may be an oxide of a metal or metalloid, such as an oxide of one or more of silicon, aluminum, titanium, cerium, or combinations of these. The catalyst support material may be silica, fumed silica, alumina, fumed alumina, titania, fumed titania, ceria, fumed ceria, or combinations of these.

In one or more embodiments, the catalyst support material may be silica. Examples of silica catalyst support materials suitable for use in preparing the composite catalyst may include mesoporous silica supports. The mesoporous silica supports may have an average pore diameter from 2.5 nanometers (nm) to 40 nm and a total pore volume of at least 0.600 milliliter per gram (mL/g). In one or more embodiments, silica of the catalyst support material may have an average pore diameter of from 2.5 nm to 40 nm, or from 2.5 nm to 20 nm, or from 2.5 nm to 4.5 nm, or from 2.5 nm to 3.5 nm, or from 8 nm to 18 nm, or from 12 nm to 18 nm. The silica supports suitable for the catalyst support material may have a total pore volume of from 0.600 mL/g to 2.5 mL/g, or from 0.600 mL/g to 1.5 mL/g, or from 0.600 mL/g to 1.3 mL/g, or from 0.600 mL/g to 0.800 mL/g, or from 0.600 mL/g to 0.700 mL/g, or from 0.900 mL/g to 1.3 mL/g. Silica supports suitable for the catalyst support material may have a surface area of from 250 square meters per gram ($m^2$/g) to 600 $m^2$/g. The silica supports may have a surface area of from 450 $m^2$/g to 600 $m^2$/g, or from 250 $m^2$/g to 500 $m^2$/g, or from 275 $m^2$/g to 400 $m^2$/g, or from 275 $m^2$/g to 350 $m^2$/g.

In one or more than one embodiments, the silica supports may be substantially free of extraneous metals or elements which might adversely affect the catalytic activity of the system. As used in the present disclosure, the term "substantially free" of a component may refer to a composition, such as a catalyst support material, zeolite, catalyst or catalyst precursor mixture, having less than 1 weight percent (wt. %) of that component in the composition. For example, the silica supports that are substantially free of extraneous metals or elements may contain less than 1 wt. % of these extraneous metals or elements. One suitable silica support may be the Santa Barbara Amorphous (SBA-15) mesoporous silica molecular sieve. Alternatively, another suitable example of a silica support may be the CARiACT® silica support (commercially available from Fuji Silysia Chemical Ltd, headquartered in Aichi, Japan). In one or more embodiments, catalyst support material can be CARiACT® Grade Q-10 silica support particles having an average pore diameter of 10 nm, a pore volume of 1 mL/g, a surface area of 300 $m^2$/g, and an average particle size of from 75 micrometers (μm) to 150 μm. In one or more embodiments, the catalyst support material can be CARiACT® Grade Q-10 silica particles with average particle sizes of from 75 μm to 500 μm.

The composite catalyst and methods of making the composite catalyst of the present disclosure utilize preformed catalyst support particles, such as silica or other metal oxide particles, for the catalyst support material instead of other sources of catalyst supports. Thus, the methods of the present disclosure for preparing the composite catalysts may not include the step of forming the catalyst support materials from one or more precursors, such as preparing silica from one or more silica precursors, prior to spray drying, during the spray drying process, or during an additional calcination step. The initial provision of the preformed catalyst support material with optimal properties of surface area, pore diameter, and pore volume leads to the reliable formation of a uniform catalyst composition. The use of silicon dioxide precursors, such as tetraethyl orthosilicate, requires additional steps of formation of $SiO_2$ in the spray dryer and does not result in uniform support structures. Additionally, when silica precursors are used, at least a portion of the catalytically active compound precursor may be trapped within the silica rather than being deposited on the surfaces of the silica, which can render this portion of the catalytically active compounds unusable and can increase the amount of the expensive catalytically active compound precursors required. Thus, the propylene selectivity and yield in the metathesis reactions are affected.

The composite catalyst may include an amount of the catalyst support material sufficient to form agglomerates that partially or fully surround and entrap the zeolite particles within the agglomerates of the catalyst support material. The composite catalyst may have from 20 wt. % to 90 wt. % catalyst support material based on the total weight of the composite catalyst. The composite catalyst may include from 20 wt. % to 85 wt. %, from 20 wt. % to 80 wt. %, from 20 wt. % to 75 wt. %, from 20 wt. % to 70 wt. %, from 20 wt. % to 60 wt. %, from 30 wt. % to 90 wt. %, from 30 wt. % to 85 wt. %, from 30 wt. % to 80 wt. %, from 30 wt. % to 75 wt. %, from 30 wt. % to 70 wt. %, from 50 wt. % to 90 wt. %, from 50 wt. % to 85 wt. %, from 50 wt. % to 80 wt. %, from 50 wt. % to 75 wt. %, from 50 wt. % to 70 wt. %, from 60 wt. % to 90 wt. %, from 60 wt. % to 85 wt. %, or from 60 wt. % to 85 wt. % catalyst support material based on the total weight of the composite catalyst.

As previously discussed, the composite catalyst may further include zeolite particles that are at least partially or fully surrounded by or embedded in the catalyst support material. The zeolite particles may include one or more than one zeolite composition. As used in the present disclosure, a zeolite composition refers to a zeolite with a particular zeolitic framework structure and having a particular material composition. Thus, zeolite compositions may differ between one another by framework structure, composition, or both. Zeolite compositions may be grouped into "zeolite types" such as MFI framework type zeolites (such as ZSM-5 zeolite), FAU framework type zeolites (such as Y zeolite), or *BEA framework type zeolites (such as zeolite Beta), each of which is described subsequently in this disclosure. Other zeolite types having other framework types and compositions may also be used to produce the composite catalyst.

In one or more embodiments, the zeolite particles may comprise one or more MFI framework type zeolites, such as ZSM-5. As used in the present disclosure, "ZSM-5" refers to zeolites having an MFI framework type according to the International Union of Pure and Applied Chemistry (IUPAC) zeolite nomenclature and consisting of silica and alumina. ZSM-5 refers to "Zeolite Socony Mobil-5" and is a pentasil family zeolite that can be represented by the chemical formula $Na_n$—$Al_n$—$Si_{96-n}O_{192}.16H_2O$, where $0<n<27$. Examples of commercially available zeolite ZSM-5 may include but are not limited to CBV2314, CBV3024E, CBV5524G and CBV28014 (available from Zeolyst International). The MFI framework type zeolite may comprise one or more phosphorous-containing compounds, such as a phosphorous oxide, such as phosphorous pentoxide ("$P_2O_5$").

In one or more embodiments, the catalyst composition may comprise a FAU framework type zeolite, such as zeolite Y. As used in this disclosure, "zeolite Y" refers to zeolite having a FAU framework type according to the IUPAC zeolite nomenclature and consisting of silica and alumina, where the molar ratio of silica to alumina is at least 3. For example, the molar ratio of silica to alumina in the zeolite Y may be at least 5, at least 12, or even at least 30, such as from 5 to 30, from 12 to 30, or from about 15 to about 30. The unit cell size of the zeolite Y may be from about 24 Angstrom to about 25 Angstrom, such as 24.56 Angstrom.

In one or more embodiments, the catalyst composition may comprise one or more *BEA framework type zeolites, such as zeolite Beta. As used in this disclosure, "zeolite Beta" refers to zeolite having a *BEA framework type according to the IUPAC zeolite nomenclature and consisting of silica and alumina. The molar ratio of silica to alumina in the zeolite Beta may be at least 10, at least 25, or even at least 100. For example, the molar ratio of silica to alumina in the zeolite Beta may be from 5 to 500, such as from 25 to 300. Examples of commercially available zeolite Beta compositions may include, but are not limited to, CP814C, CP814E and CP811C-300 (produced by Zeolyst International). The zeolite Beta may be in the form of H-Beta. H-Beta refers to the acidic form of zeolite Beta usually derived from ammonium-Beta ($NH_4$-Beta) via calcination. In one or more embodiments, the zeolite Beta may be stabilized by direct reaction with phosphoric acid ($H_3PO_4$) or by impregnation with ammonium hydrogen phosphate (($NH_4)_2HPO_4$). According to one or more embodiments, the *BEA framework type zeolite may comprise one or more phosphorous-containing compounds, such as a phosphorous oxide or phosphorous pentoxide ("$P_2O_5$").

The zeolite particles may have a weight ratio of silica to alumina of from 10:1 to 6000:1. For example, the zeolite may have a weight ratio of silica to alumina of from 10:1 to 4000:1, from 10:1 to 2000:1, from 10:1 to 1000:1, from 10:1 to 500:1, from 10:1 to 300:1, from 100:1 to 6000:1, from 100:1 to 4000:1, from 100:1 to 2000:1, from 100:1 to 1000:1, from 100:1 to 500:1, from 200:1 to 6000:1, from 200:1 to 4000:1, from 200:1 to 2000:1, from 200:1 to 1000:1, from 200:1 to 500:1, from 500:1 to 6000:1, from 500:1 to 4000:1, from 500:1 to 2000:1, from 500:1 to 1000:1, from 1000:1 to 6000:1, from 1000:1 to 4000:1, or from 1000:1 to 2000:1, based on the total weight of the zeolite. In one or more embodiments, the zeolite particles may be an MFI 2000 zeolite cracking catalyst having a weight ratio of silica to alumina of 2000:1.

The zeolite particles may have an average particle size less than the average particle size of the composite catalyst. The zeolite particles may have an average particle size of less than or equal to 35 µm, less than or equal to 30 µm, less than or equal to 25 µm, or even less than or equal to 20 µm. The zeolite particles may have an average particle size of greater than or equal to 5 µm, greater than or equal to 10 µm, or even greater than or equal to 15 µm. The zeolite particles may have an average particle size of from 5 µm to 35 µm, from 5 µm to 30 µm, from 5 µm to 25 µm, from 5 µm to 20 µm, from 10 µm to 35 µm, from 10 µm to 30 µm, from 10 µm to 25 µm, from 10 µm to 20 µm, from 15 µm to 35 µm, from 15 µm to 30 µm, from 15 µm to 25 µm, from 15 µm to 20 µm, from 5 µm to 10 µm, or even from 5 µm to 20 µm.

The composite catalyst may include an amount of the zeolite particles sufficient to catalyst cracking reactions during metathesis of butene to produce propene and other light olefins. The composite catalyst may include from 5 wt. % to 50 wt. % zeolite particles based on the total weight of the composite catalyst. The composite catalyst may include from 5 wt. % to 40 wt. %, from 5 wt. % to 30 wt. %, from 10 wt. % to 50 wt. %, from 10 wt. % to 40 wt. %, from 10 wt. % to 30 wt. %, from 15 wt. % to 50 wt. %, from 15 wt. % to 40 wt. %, from 15 wt. % to 30 wt. %, or from 20 wt. % to 30 wt. % zeolite particles based on the total weight of the composite catalyst.

In some embodiments, the composite catalyst particles of the present disclosure may be agglomerations of the catalyst support material and the zeolite particles. For example, the catalyst support material and zeolite particles may form agglomerates in which the zeolite particles are at least partially or fully embedded in the catalyst support material. Additionally, a catalytically active compound may be deposited on surfaces throughout the composite catalyst particles and may produce catalytically active sites at outer surfaces and pore surfaces of the catalyst support material, the zeolite particles, or both.

As previously described, the composite catalyst may have at least one catalytically active compound supported by the catalyst support material, the zeolite particles, or both. The catalytically active compound is different from the zeolite particles and the catalyst support material. The catalytically active compounds may include compounds that have catalytic activity to promote metathesis reactions, isomerization reactions, or both. The catalytically active compounds may also be functional to remove contaminants and catalyst poisons from a reactant stream. The catalytically active compounds may include a metathesis catalyst. In one or more embodiments, the catalytically active compounds may include an isomerization catalyst.

The catalytically active compound may be a metal, metal oxide, other catalytically active compound, or combinations of these. The catalytically active compound may be a metal, such as but not limited to platinum, gold, palladium, rhodium, iridium, chromium, other metal, or combinations of these. The catalytically active compound may include a metal oxide, such as one or more than one oxide of a metal from Groups 6-10 of the International Union of Pure and Applied Chemistry Periodic Table of the Elements (IUPAC periodic table). The metal oxide may include at least one oxide of molybdenum, rhenium, tungsten, manganese, titanium, cerium, or any combination of these. In some embodiments, the metal oxide may be tungsten oxide. The morphology, type, and amount of the catalytically active compound deposited on the surface of the catalyst support may determine the catalytic activity of the composite catalyst.

The composite catalyst may include one or a plurality of catalytically active compounds supported by the catalyst support material, the zeolite particles, or both. For example, the composite catalyst may include 1, 2, 3, 4, 5, 6, or more than 6 catalytically active compounds. Theoretically, the number of different catalytically active compounds that can be incorporated into the composite catalyst may be unlimited. However, the number of different catalytically active compounds that can be included in the composite catalyst may be limited by the type of reactions that can be conducted simultaneously. The number of different catalytically active compounds may also be limited by reactions that must be conducted sequentially. The number of different catalytically active compounds may also be limited by catalyst poisoning considerations.

The catalytically active compounds may be disposed at the surfaces of the composite catalyst that are accessible to vapors and gases, such as being deposited on the outer surfaces and pore surfaces of the composite catalyst. The catalytically active compounds may be deposited on the outer surfaces or pore surfaces of the catalyst support material, the zeolite particles, or both. The catalytically active compounds may provide catalytically active sites at the surfaces of the composite catalyst, such as the outer surfaces, pore surfaces, or both.

The composite catalyst may have an amount of the catalytically active compounds sufficient for the composite catalyst to exhibit the functionality of the catalytically active compound. For example, the catalytically active compound may be tungsten oxide, and the composite catalyst may include an amount of the tungsten oxide sufficient to catalyze olefin metathesis reactions. The composite catalyst may include from 0.1 wt. % to 25 wt. % catalytically active compound based on the total weight of the composite catalyst. The composite catalyst may have from 0.1 wt. % to 20 wt. %, from 0.1 wt. % to 15 wt. %, from 0.1 wt. % to 10 wt. %, from 0.1 wt. % to 8 wt. %, from 1 wt. % to 25 wt. %, from 1 wt. % to 20 wt. %, from 1 wt. % to 15 wt. %, from 1 wt. % to 10 wt. %, from 1 wt. % to 8 wt. %, from 4 wt. % to 25 wt. %, from 4 wt. % to 20 wt. %, from 4 wt. % to 15 wt. %, from 4 wt. % to 10 wt. %, from 4 wt. % to 8 wt. %, from 8 wt. % to 25 wt. %, from 8 wt. % to 20 wt. %, from 8 wt. % to 15 wt. %, from 6 wt. % to 8 wt. %, from 6 wt. % to 10 wt. %, or from 6 wt. % to 15 wt. % catalytically active compound based on the total weight of the composite catalyst.

The composite catalysts of the present disclosure may be synthesized through a spray drying process. In the spray drying process, a catalyst precursor mixture may be prepared and then introduced to a spray dryer. The catalyst precursor mixture may prepared by combining the zeolite particles, the catalyst support material, a catalytically active compound precursor, a surfactant, and at least one diluent to form a catalyst precursor composition and then mixing the catalyst precursor composition to produce the catalyst precursor mixture. The zeolite particles may be any of the zeolites previously described in the present disclosure. For example, in one or more embodiments, the zeolite particles may be ZSM-5 zeolite particles. The catalyst precursor mixture may include from 5 weight percent (wt. %) to 50 wt. % zeolite particles based on the dry weight of the catalyst precursor mixture. As used throughout the present disclosure, the "dry weight" of the catalyst precursor mixture refers to the total weight of the catalyst precursor mixture minus the total weight of diluents in the catalyst precursor mixture.

The catalyst support material may be any of the catalyst support materials previously described in the present disclosure. For example, in one or more embodiments, the catalyst support material may include one or more of silica, alumina, titania, ceria, or combinations of these. In one or more embodiments, the catalyst support material may be silica supports, such as preformed silica support particles, which may have any of the features, characteristics, or properties previously described for the silica supports. The catalyst precursor mixture may include from 20 wt. % to 90 wt. % catalyst support material based on the dry weight of the catalyst precursor mixture. Again, dry weight refers to the weight of the catalyst precursor mixture 108 without the diluent. For example, in some embodiments, the catalyst precursor mixture 108 may include from 20 wt. % to 85 wt. %, from 20 wt. % to 80 wt. %, from 20 wt. % to 75 wt. %, from 20 wt. % to 70 wt. %, from 20 wt. % to 60 wt. %, from 30 wt. % to 90 wt. %, from 30 wt. % to 85 wt. %, from 30 wt. % to 80 wt. %, from 30 wt. % to 75 wt. %, from 30 wt. % to 70 wt. %, from 50 wt. % to 90 wt. %, from 50 wt. % to 85 wt. %, from 50 wt. % to 80 wt. %, from 50 wt. % to 75 wt. %, from 50 wt. % to 70 wt. %, from 60 wt. % to 90 wt. %, from 60 wt. % to 85 wt. %, or from 60 wt. % to 80 wt. % catalyst support material based on the dry weight of the catalyst precursor mixture.

The catalytically active compound precursor may be a metal, such as platinum, gold, palladium, rhodium, iridium, chromium, other metal, or combinations of these. Alternatively or additionally, the catalytically active compound precursors may include a metal salt that can be solubilized in the diluent. The catalytically active compound precursors may include an oxometallate precursor. The oxometallate precursor may be a metal oxide precursor of one or more oxides of a metal from the Groups 6-10 of the IUPAC Periodic Table. The metal oxide may be at least one oxide of molybdenum, rhenium, tungsten, manganese, titanium, cerium, or any combination of these. Alternatively, the oxometallate precursor may be a tungstate precursor. Examples of tungstate precursors may include, but are not limited to, ammonium metatungstate $((NH_4)_6H_2W_{12}O_{40})$, ammonium paratungstate, tungstic acid, phosphotungstic acid, sodium tungstate, other tungstate precursor, or combinations of these. In one or more embodiments, the tungstate precursor may comprise ammonium metatungstate, ammonium metatungstate hexahydrate, or ammonium paratungstate. In one or more embodiments, the oxometallate precursor may be a tungsten oxide, such as tungsten (IV) oxide, tungsten (VI) oxide, other tungsten oxides, or combinations of tungsten oxides. In one or more embodiments, the metal oxide is tungsten oxide ($WO_3$). The catalyst precursor mixture may include a plurality of catalytically active compound precursors to produce a composite catalyst having a plurality of catalytically active compounds deposited on the outer and pore surfaces of the catalyst support material, zeolite particles, or both.

The catalyst precursor mixture may include from 0.1 wt. % to 25 wt. % catalytically active compound precursors, based on the dry weight of the catalyst precursor mixture. The catalyst precursor mixture may include from 0.1 wt. % to 20 wt. %, from 0.1 wt. % to 15 wt. %, from 0.1 wt. % to 10 wt. %, from 0.1 wt. % to 8 wt. %, from 1 wt. % to 25 wt. %, from 1 wt. % to 20 wt. %, from 1 wt. % to 15 wt. %, from 1 wt. % to 10 wt. %, from 1 wt. % to 8 wt. %, from 4 wt. % to 25 wt. %, from 4 wt. % to 20 wt. %, from 4 wt. % to 15 wt. %, from 4 wt. % to 10 wt. %, from 4 wt. % to 8 wt. %, from 8 wt. % to 25 wt. %, from 8 wt. % to 20 wt. %, from 8 wt. % to 15 wt. %, from 6 wt. % to 8 wt. %, from 6 wt. % to 10 wt. %, or from 6 wt. % to 15 wt. % catalytically active compound precursors, based on the dry weight of the catalyst precursor mixture.

A polymeric surfactant may be included in the catalyst precursor mixture to enhance the dispersion of the catalytically active compound precursor in the catalyst precursor mixture, resulting in improved distribution of the catalytically active compound on the surfaces of the catalyst support material, zeolite particles, or both. The surfactant may be a symmetric triblock copolymer surfactant, such as the Pluronic® P123 surfactant (available from BASF Corporation, headquartered in Florham Park, N.J., USA), which is a poly(ethylene glycol)-block-poly(propylene glycol)-block-poly(ethylene glycol) copolymer (PEG-PPG-PEG copolymer). The triblock copolymer, PEG-PPG-PEG, comprises of poly(ethylene oxide)(PEO) and poly (propylene oxide) (PPO) comonomers and exhibits hydrophobicity at temperatures above 288 Kelvin and solubility in water at temperatures below 288 Kelvin. This dual characteristic leads to formation of micelles including of PEG-PPG-PEG triblock copolymers. Dissolved Pluronic® P123 surfactant forms micelles that are used as the backbone to make structured mesoporous silica such as SBA-15. In contrast, disclosed here are uses of the triblock copolymer to facilitate the deposition of the catalytically active compound, such as tungsten oxide, on the catalyst support material. In a conventional synthesis, the surfactant is added to a metal precursor and this mixture is subject to thermal treatment. The metal precursor decomposes to generate a metal oxide. In the methods and compositions of the present disclosure, the surfactant may be used to enhance the mixing between the catalyst support material, such as a silica support, and the catalytically active compound precursor, such as tungsten precursor, in the catalyst precursor mixture. The enhanced mixing provided by the surfactant may improve the distribution of the catalytically active compound (such as tungsten oxide) on the surfaces of the catalyst support material and zeolite particles, upon thermal treatment. Surfactant properties, such as whether the surfactant is ionic, cationic, or nonionic, play a role in the effectiveness of a polymeric surfactant. The use of a triblock copolymer enables an easy and reliable large-scale method of preparation of the composite catalysts of the present disclosure.

The catalyst precursor mixture may have an amount of surfactant sufficient to evenly disperse the catalytically active compound precursor throughout the catalyst precursor mixture. The catalyst precursor mixture may include from 1 wt. % to 20 wt. % surfactant based on the dry weight of the catalyst precursor mixture. The catalyst precursor mixture may include from 1 wt. % to 15 wt. %, from 1 wt. % to 18 wt. %, from 1 wt. % to 15 wt. %, from 5 wt. % to 20 wt. %, from 5 wt. % to 18 wt. %, from 5 wt. % to 15 wt. %, from 8 wt. % to 20 wt. %, from 8 wt. % to 18 wt. %, from 8 wt. % to 15 wt. %, from 10 wt. % to 20 wt. %, from 10 wt. % to 18 wt. %, or from 10 wt. % to 15 wt. % surfactant based on the dry weight of the catalyst precursor mixture.

The diluent may be water, an organic solvent, or a combination of water and at least one organic solvent. Example organic solvents may include methanol, ethanol, acetone, or a combination of solvents. In one or more embodiments, the diluent may be water such that the catalyst precursor mixture is an aqueous catalyst precursor mixture. The diluent may also include water in combination with an alcohol, such as ethanol, which may improve the ability to dissolve the triblock copolymer surfactant in the diluent during preparation of the catalyst precursor mixture. The catalyst precursor mixture may have an amount of the diluent sufficient to atomize the catalyst precursor mixture in the spray dryer. The catalyst precursor mixture may have an amount of diluent sufficient to produce a desired average particle size of the composite catalyst particles made by the spray drying process. For example, increasing the amount of diluent may decrease the average particle size of the composite catalyst due to the decreased concentration of the catalyst support material, zeolite particles, catalytically active compound precursor, and surfactant in each of the droplets. The catalyst precursor mixture may include from 50 wt. % to 95 wt. % diluent based on the total weight of the catalyst precursor mixture. For example, the catalyst precursor mixture may include from 50 wt. % to 90 wt. %, from 50 wt. % to 85 wt. %, from 50 wt. % to 80 wt. %, from 70 wt. % to 95 wt. %, from 70 wt. % to 90 wt. %, from 70 wt. % to 85 wt. %, from 80 wt. % to 95 wt. %, or from 80 wt. % to 90 wt. % diluent based on the total weight of the catalyst precursor mixture.

Referring to FIG. 1, the catalyst precursor mixture, designated in FIG. 1 by reference number 142, may be prepared by combining the catalyst support material, the zeolite particles, the catalytically active compound precursor, the triblock copolymer surfactant, and the diluent to form a catalyst precursor composition and then mixing the catalyst precursor composition to produce the catalyst precursor mixture. The catalyst precursor composition may be prepared through one or a plurality of mixing processes. Preparation of the catalyst precursor mixture 142 may include a first mixing process 102 that may include combining the zeolite particles 104, the catalyst support material 105, and a first portion 106 of the diluent to produce a first mixture 108. The first mixing process 102 may further include mixing the first mixture 108 under conditions sufficient to disperse the solid zeolite particles and solid catalyst support materials in the diluent. The first mixing process 102 may be conducted in a vessel having a mixer or agitator. In one or more embodiments, the vessel may be a feed vessel for the spray dryer 150. The first mixture 108 may be mixed at a rotational speed of greater than or equal to 600 rotations per minute (rpm), greater than or equal to 700 rpm, or even greater than or equal to 800 rpm, such as from 800 rpm to 1200 rpm. The first mixture 108 may be mixed for at least 30 minutes, such as from 30 minutes to 24 hours.

Preparation of the catalyst precursor mixture 142 may include a second mixing process 110, in which the surfactant 112, such as the triblock copolymer surfactant, may be combined with a second portion 114 of the diluent and mixed until the surfactant is completely dissolved in the diluent to produce a second mixture 118. When the surfactant is a triblock copolymer surfactant, the second portion 114 of the diluent may include an alcohol 116, such as ethanol for example, which may be added to the second portion 114 of the diluent. The ethanol 116 may assist in dissolving the surfactant 112 to form a homogeneous second mixture 118. The second mixture 118 may be prepared in a vessel having a mixer or agitator and may be mixed under conditions sufficient to completely dissolve the surfactant 112 in the diluent. For example, the second mixture 118 may be mixed at a rotational speed of greater than or equal to 600 rpm, greater than or equal to 700 rpm, or greater than or equal to 800 rpm, such as from 600 rpm to 2000 rpm or from 700 rpm to 1500 rpm. The second mixture 118 may be mixed for a time period of at least 30 minutes, such as from 30 minutes to 24 hours.

Preparation of the catalyst precursor mixture 142 may further include a third mixing process 110, in which at least one catalytically active compound precursor 122 may be combined with a third portion 124 of the diluent, such as water, and mixed until the catalytically active compound precursor 122 completely dissolves in the third portion 124 of the diluent to produce a third mixture 128. The third mixture 128 may be prepared in a vessel having a mixer or agitator and may be mixed under conditions sufficient to completely dissolve the catalytically active compound precursor 122 in the diluent. For example, the third mixture 128 may be mixed at a rotational speed of greater than or equal to 600 rpm, greater than or equal to 700 rpm, or greater than or equal to 800 rpm, such as from 600 rpm to 2000 rpm or from 700 rpm to 1500 rpm. The third mixture 128 may be mixed for a time period of at least 30 minutes, such as from 30 minutes to 24 hours.

Referring still to FIG. 1, preparation of the catalyst precursor mixture 142 may include combing the second mixture 118 and the third mixture 128 to produce a fourth mixture 132 that includes the surfactant 112 and the at least one catalytically active compound precursor 122 dissolved in the diluent. The fourth mixture 132 may be mixed under conditions sufficient to produce a homogeneous mixture of the surfactant and catalytically active compound precursor.

The fourth mixture 132 may be added to the first mixture 108, which includes the zeolite particles and catalyst support material dispersed in the diluent to produce the catalyst precursor composition. The fourth mixture 132 and first mixture 108 may be combined in the feed vessel 140 of the spray dryer 150. The catalyst precursor composition may be mixed to produce the catalyst precursor mixture 142 in which the catalyst support material and the zeolite particles are suspended in the diluent and do not precipitate or settle out of the catalyst precursor mixture 142 during spray drying. The catalyst precursor composition may be mixed under conditions sufficient to reduce or prevent precipitation or settling of the catalyst support material, zeolite particles, or both, during spray drying. The catalyst precursor composition may be mixed at a rotational speed of up to 700 rpm, such as from 500 rpm to 700 rpm. The catalyst precursor composition may be mixed for a period of time sufficient to produce the catalyst precursor mixture which may be a colloidal mixture in which the catalyst support particles, zeolite particles, or both do not precipitate or settle out during spray drying. The catalyst precursor composition may be mixed for a period of time greater than or equal to 72 hours, such as from 72 hours to 120 hours or from 72 hours to 96 hours to produce the catalyst precursor mixture 142. After mixing, the catalyst precursor mixture 142 may be colloidal solution, which may be a stable mixture. In other words, after mixing, the catalyst precursor mixture 142 may be a homogeneous colloidal mixture that may have a reduced propensity for solids dropping out of solution and settling compared to the catalyst precursor composition before mixing. When the mixing time is less than 72 hours, the catalyst precursor mixture 142 may not form a stable colloidal solution and may exhibit settling of the catalyst support material during spray drying, which may adversely affect the composite catalyst produced by the process. This settling may affect the efficiency of the spray drying process, which may decrease the product yield when the composite catalyst is used in a metathesis process.

The catalyst precursor mixture 142 may include from 20.0 wt. % to 85.0 wt. % catalyst support material 104, from 5.0 wt. % to 50.0 wt. % zeolite particles 105, from 1 wt. % to 20 wt. % surfactant, and from 0.1 wt. % to 25.0 wt. % catalytically active compound precursors, based on the dry weight of the catalyst precursor mixture. The catalyst precursor mixture 142 may have an amount of solids of from 1 wt. % to 50 wt. %, from 1 wt. % to 30 wt. %, from 1 wt. % to 20 wt. %, from 5 wt. % to 50 wt. %, from 5 wt. % to 30 wt. %, from 5 wt. % to 20 wt. %, from 10 wt. % to 50 wt. %, from 10 wt. % to 30 wt. %, from 10 wt. % to 20 wt. %, from 15 wt. % to 50 wt. %, from 15 wt. % to 30 wt. %, from 15 wt. % to 20 wt. %, or from 20 wt. % to 50 wt. % based on the total weight of the catalyst precursor mixture 142, where the solids comprise the zeolite particles, catalyst support material, catalytically active compound precursor, and copolymer surfactant (everything but the diluents).

Referring again to FIG. 1, the catalyst precursor mixture 142 may be spray dried in a spray dryer 150 to produce the composite catalyst. The spray dryer 150 may be any commercially-available spray dryer system. The spray dryer 150 may include a drying chamber 151 that includes a cylindrical portion 152 and a conical portion 154. The spray dryer 150 may also include a spray nozzle 156 disposed within the drying chamber 151 and operable to atomize the catalyst precursor solution 142 within the drying chamber 151. A heated gas 144 may be introduced to the drying chamber 151. The gas may be air or an inert gas, such as but not limited to nitrogen, helium, argon, or other inert gas. Additionally, water 146 may be fluidly coupled to the spray nozzle 156 for use during start-up of the spray dryer 150. The catalyst precursor mixture 142 may be heated to a spraying temperature prior to introducing the catalyst precursor mixture 142 to the spray nozzle 156. The spraying temperature of the catalyst precursor mixture 142 may be greater than or equal to 50° C., greater than or equal to 75° C., or even greater than or equal to 100° C. The spraying temperature of the catalyst precursor mixture may be from 50° C. to 150° C., from 50° C. to 125° C., from 75° C. to 150° C., from 75° C. to 125° C., from 100° C. to 150° C., or even from 100° C. to 125° C. If the spraying temperature is too low, evaporation of the diluent from the droplets of catalyst precursor mixture 142 in the drying chamber 151 may be insufficient at the surface temperature of the drying chamber 151. If the spraying temperature is too high, evaporation of the diluent may be too rapid, resulting in reduced cohesion within the composite catalyst, which can influence the durability of the composite catalyst.

During steady-state operation of the spray dryer 150, the catalyst precursor mixture 142 may be delivered to the spray nozzle 156 by catalyst precursor pump 143. The spray nozzle 156 may atomize the catalyst precursor mixture 142 into a plurality of droplets of the catalyst precursor mixture 142. The type of spray nozzle 156 may influence the average droplet size of the droplets of catalyst precursor mixture 142 in the drying chamber 151, which may influence the average particle size of the composite catalyst recovered from the spray dryer 150. For example, a spray nozzle 156 configured to produce smaller-sized droplets may produce composite catalysts having a smaller average particle size. Additionally, the pressure, flowrate, or both, of the catalyst precursor mixture 142 delivered to the spray nozzle 156 may also influence the droplet size and the average particle size of the composite catalyst.

Referring to FIG. 1, the droplets of the catalyst precursor mixture 142 are atomized into the spray drying chamber 151, where the droplets are heated by the heated gas 144. The drying chamber 151 of the spray dryer 150 may be maintained at a surface temperature sufficient to vaporize the diluent 106 from the droplets of the catalyst precursor mixture 142 to form a plurality of solid composite catalyst particles. The surface temperature of the drying chamber 151 refers to the temperature measured at the interior surface of the drying chamber 151. The heated gas 144 may be heated to a temperature sufficient to maintain the surface temperature of the drying chamber 151. The drying chamber 151 may be maintained at a surface temperature of from 200° C. to 300° C., such as from 200° C. to 285° C., from 200° C. to 280° C., from 200° C. to 275° C., from 250° C. to 300° C., from 250° C. to 285° C., from 250° C. to 280° C., from 250° C. to 275° C., from 260° C. to 300° C., from 260° C. to 285° C., from 260° C. to 280° C., or from 260° C. to 275° C. If the surface temperature of the drying chamber is too low, then the diluent in the droplets of catalyst precursor mixture 142 may not completely vaporize to produce the solid composite catalyst particles.

In the drying chamber 151, heat from the heated gas 144 may cause removal of the diluents from the droplets of the catalyst precursor mixture 142, such as by vaporization of the diluents. As the diluent vaporizes from the droplets of the catalyst precursor mixture 142, the volume of each of the droplets of the catalyst precursor mixture 142 may decrease, and the catalyst support material of the catalyst support precursor 142 may converge to form agglomerates that may at least partially or fully surround and secure or trap the zeolite particles within the catalyst support material to form the composite catalyst particles.

As the diluent is removed, the catalytically active compound precursor may deposit onto the surfaces of the catalyst support material, the zeolite particle, or both. The triblock copolymer surfactant in the catalyst precursor mixture may operate to space apart the catalytically active compound precursor and prevent consolidation of the catalytically active compound precursor into larger crystals or agglomerates during the drying process. This may enable the catalytically active compound precursor to be more evenly distributed across the surfaces (outer and pore surfaces) of the catalyst support material, zeolite particles, or both. As the diluent is removed from the droplets of the catalyst precursor mixture 142 in the drying chamber 151, the catalytically active compound precursor depositing on the surfaces of the catalyst support material, zeolite particles, or both may undergo chemical reaction to transition from the catalytically active compound precursor into the catalytically active compound. For example, a catalytically active compound precursor comprising a tungsten compound, such as ammonium metatungstate, may undergo oxidation at the temperatures in the drying chamber 151 to convert the tungsten compound to tungsten oxide. Thus, the composite catalyst recovered from the drying chamber 151 of the spray dryer 150 may include the catalytically active compound deposited on the outer and pore surfaces of the catalyst support material, the zeolite particles, or both.

Referring again to FIG. 1, the spray dryer 150 may include one or a plurality of catalyst outlets in the drying chamber 151, each outlet fluidly coupled to a solid separator and blower 190 operable to pull air and spray dried composite catalyst out of the drying chamber 151. A first composite catalyst stream 160 may be removed from a first outlet disposed at a converging end of the conical portion 154 of the drying chamber 151. The converting end of the conical portion 154 may be disposed at a bottom end of the drying chamber 151 so that the first outlet is at the bottom of the drying chamber 151. Composite catalyst spray dried in the drying chamber 151 may eventually descend to the conical portion 154 of the drying chamber 151. The first composite catalyst stream 160 may be passed out of the drying chamber 151 and to a first solid separator 170. The first solid separator 170 may be fluidly coupled to the blower 190, which may be operable to pull the first composite catalyst stream 160 comprising composite catalyst and heated air out of the drying chamber 151 from the first catalyst outlet and transfer the first composite catalyst stream 160 to the first solid separator 170. The first solid separator 170 may be operable to separate a first composite catalyst 180 from the heated air in the first composite catalyst stream 160. The first solid separator 170 may be a cyclonic separator, filter, or other solid-gas separation device. The first composite catalyst 180 may be recovered from the first solid separator 170. The heated gas may be drawn through the first solid separator by the blower 190 and removed from the process.

A second composite catalyst stream 162 may be removed from a second outlet of the drying chamber 151. The second outlet may be disposed upstream of the first outlet relative to the flow of the composite catalyst downward through the drying chamber 151. The second outlet may be disposed in the cylindrical section 152 of the drying chamber 151 or proximate a diverging end of the conical portion 154 of the drying chamber 151. As the droplets of the catalyst precursor mixture 142 transition to solid composite catalyst particles in the drying chamber 151, the heavier solid composite catalyst particles may descend more rapidly downward in the −Z direction of the coordinate axis in FIG. 1 compared to the lighter solid composite catalyst particles. As used throughout this disclosure, "heavier" composite catalyst particles may refer to composite catalyst particles that have greater density or greater average particle size compared to "lighter" composite catalyst particles. Thus, during steady state operation of the spray dryer 150, a gradient in particle density, average particle size, or both, may form in drying chamber 151 in the vertical direction (+/−Z direction of the coordinate axis in FIG. 1). Removing the composite catalyst from different vertical positions of the drying chamber 151 may enable recovery of composite catalysts with different average particles sizes, different densities, or both. Generally, removing the composite catalyst particles from a higher position (in a greater+Z position) within the drying chamber 151 may produce a composite catalyst stream that includes composite catalyst having a lesser density, average particle size, or both, compared to the first composite catalyst 180 recovered from the bottom of the drying chamber 151.

The second composite catalyst stream 162 may be passed out of the drying chamber 151 and to a second solid separator 172. The second solid separator 172 may be fluidly coupled to the blower 190, which may be operable to pull the second composite catalyst stream 162 comprising composite catalyst and heated air out of the drying chamber 151 from the second catalyst outlet and transfer the second composite catalyst stream 162 to the second solid separator 172. The second solid separator 172 may be operable to separate a second composite catalyst 182 from the heated gas in the second composite catalyst stream 162. The second solid separator 172 may be a cyclonic separator, filter, or other solid-gas separation device. The second composite catalyst 182 may be recovered from the second solid separator 172. The heated gas may be drawn through the second solid separator 172 by the blower 190 and removed from the process. The second composite catalyst 182 may have a lesser density, smaller average particle size, or both, compared to the first composite catalyst 180 recovered from the bottom of the drying chamber 151. Although a first composite catalyst 180 and a second composite catalyst 182 are described, it is understood that one or a plurality of composite catalyst streams may be removed from the drying chamber at various positions to produce a plurality of composite catalysts, each having a different average particle size, average density, or both.

Following spray drying of the composite catalyst, the composite catalyst, such as the first composite catalyst, the second composite catalyst, or both, may be calcined in a calcination furnace. The calcination process may be a two-step calcination process. This two-step calcination process may ensure the decomposition of the triblock copolymer surfactant, such as the Pluronic® P123 surfactant, and also the formation of stable and active catalytically active compound from the catalytically active compound precursor. For example, calcination may ensure formation of stable and active tungsten oxide species from the tungsten precursor, such as ammonium metatungstate. Calcination may be carried out in the presence of one or more of the following gases: air, oxygen, hydrogen, and nitrogen. Calcination may be carried out at calcination temperatures of from 200° C. to 700° C. The thermal treatment conditions, including the type of gaseous environment and calcination temperature, may influence the tungsten oxide species that are formed. The type of tungsten oxide species formed influences the stability and metathesis activity of the catalyst composition, including the propylene yield. The two-step calcination process described here may produce stable tungsten oxide phases for self- and cross-metathesis. The first step of the calcination process follows the thermal decomposition of ammonium metatungstate as it is converted to tungsten oxide. In an embodiment, this first step is carried out at about 200° C. to 250° C. in the presence of air. There is a significant weight loss of the tungsten precursor. The degradation of the tungsten precursor and conversion of the tungsten precursor to tungsten oxide continues until the second step which is carried out at a calcination temperature of from 500° C. to 600° C., at which the weight loss of the tungsten precursor is stabilized and active tungsten oxide species for metathesis are formed. In one or more embodiments, the composite catalyst may be first subjected to calcination at 250° C. for 2 hours and at 550° C. for 8 hours, with a ramping rate of 1° C. per minute until the first temperature is reached and 3° C. per minute until the second temperature is reached. Although the calcination process has been described with respect to composite catalysts having tungsten oxide as the catalytically active compound, it is understood that the calcination process may be used to complete formation of composite catalysts having other catalytically active compounds.

Evaluation of the physical characteristics of the spray-dried composite catalyst revealed a uniform dispersion of the catalytically active material, such as tungsten oxide, on the outer and pore surfaces of the catalyst support material. This uniform dispersion of catalytically active material may translate to greater conversions and greater propylene and ethylene yields for the composite catalyst compared to conventional metathesis catalysts prepared by conventional techniques, such as wet impregnation or incipient wetness impregnation.

The composite catalysts prepared by spray drying according to the present disclosure may have a reduced average particle size compared to the average particle size of metathesis catalyst prepared by conventional techniques, such as wet impregnation or incipient wetness impregnation. The composite catalysts may have an average particle size of less than or equal to 80 micrometers (μm), less than or equal to 50 μm, less than or equal to 30 μm, or even less than or equal to 20 μm. The composite catalysts of the present disclosure may have an average particle size of from 1 μm to 80 μm, from 1 μm to 50 μm, from 1 μm to 30 μm, from 1 μm to 20 μm, from 5 μm to 80 μm, from 5 μm to 50 μm, from 5 μm to 30 μm, from 5 μm to 20 μm, from 8 μm to 80 μm, from 8 μm to 50 μm, from 8 μm to 30 μm, or from 8 μm to 20 μm. The average particle size may be determined through scanning electron microscopy (SEM) or other known analytical methods.

The composite catalyst comprising the zeolite particles embedded within the catalyst support material and the catalytically active compound deposited on the outer and pore surfaces of the catalyst support material, the zeolite particles, or both, may be employed in a metathesis reaction process to convert butene to propene, ethene, and other olefins. The metathesis reaction process may include a metathesis reaction in combination with isomerization of butene, cracking, or both. As shown in Reaction 1 (RXN 1), the isomerization of 2-butene to 1-butene, and the isomerization of 1-butene to 2-butene, is an equilibrium reaction, as denoted by the bi-directional arrows with single heads. The isomerization of 2-butene and 1-butene may be achieved with an isomerization catalyst. As used in the present disclosure, the term "isomerization catalyst" may refer to a catalyst that promotes isomerization of alkenes, including, for example, isomerization of 2-butenes to 1-butene. As shown in Reaction 2 (RXN 2), the cross-metathesis of 1-butene and 2-butene may produce 1-propene and 2-pentene. As used in the present disclosure, the term "cross-metathesis" may refer to an organic reaction that involves the redistribution of fragments of alkenes by the scission and regeneration of carbon-carbon double bonds. In the case of cross-metathesis between 2-butene and 1-butene, the redistribution of these carbon-carbon double bonds through metathesis produces propene and $C_5$-$C_6$ olefins. The cross-metathesis of 1-butene and 2-butene may be achieved with a metathesis catalyst, such as tungsten oxide. As used in the present disclosure, the term "metathesis catalyst" may refer to a catalyst that promotes the metathesis reaction of alkenes to form other alkenes. The metathesis catalyst may also isomerize 2-butenes to 1-butene through a "self-metathesis" reaction mechanism.

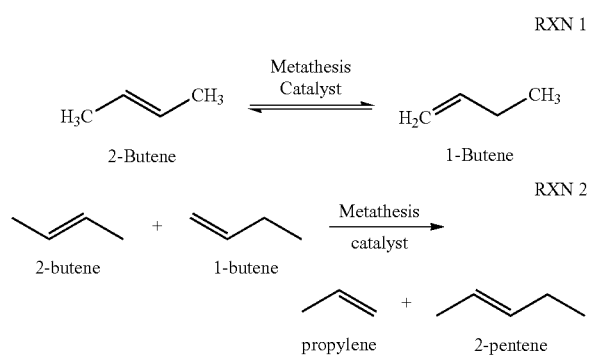

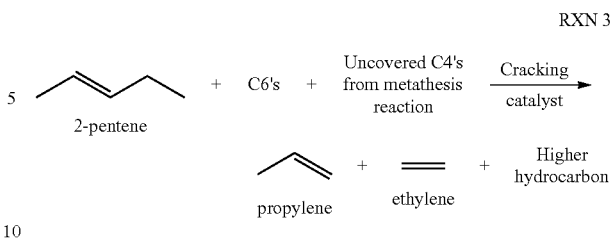

Referring to RXN 1 and RXN 2, the isomerization and metathesis reactions are not limited to these reactants and products; however, RXN 1 and RXN 2 provide a simplified illustration of the reaction methodology. As shown in RXN 2, metathesis reactions may take place between two alkenes. The groups bonded to the carbon atoms of the carbon-carbon double bond may be exchanged between the molecules to produce two new alkenes with the exchanged groups. The specific metathesis catalyst that is selected may generally determine whether a cis-isomer or trans-isomer is formed, as the formation of a cis-isomer or a trans-isomer may be, at least partially, a function of the coordination of the alkenes with the catalyst. 1-butene may also self-metathesize in the presence of a metathesis catalyst to produce ethylene and 3 hexene through similar reaction mechanisms.

Further, as shown in the following Reaction 3 (RXN 3), which is provided subsequently in this disclosure, "cracking" may refer to the catalytic conversion of C4+ alkenes to propene and other alkanes, alkenes, or alkanes and alkenes, for example, $C_2$-$C_3$ alkenes. Cracking reactions are not limited to the reactants and products shown in RXN3; however, RXN 3 provide a simplified illustration of the cracking reaction.

Butene may be converted to propene and other olefins through metathesis and cracking by contacting a butene-containing feedstock with the composite catalyst of the present disclosure at reactions conditions sufficient to conduct the metathesis reaction. In one or more embodiments, the composite catalyst may include ZSM-5 zeolite particles embedded in the catalyst support material comprising mesoporous silica. The composite catalyst may further include tungsten oxide as the catalytically active compound dispersed across the outer and pore surfaces of the mesoporous silica catalyst support, the ZSM-5 zeolite particles, or both. The metathesis process may optionally include an additional isomerization catalyst to maintain an equilibrium concentration of 1-butene and 2-butene in the reactor. The isomerization catalyst may be a separate particulate catalyst disposed upstream of the composite catalyst or mixed with the composite catalyst.

Referring now to FIG. 2, a reactor system 200 for conducting metathesis of butene is schematically depicted. The reactor system 200 may include a metathesis reactor 210 and a metathesis effluent separation system 230 downstream of the metathesis reactor 210. The metathesis reactor 210 may be a fixed bed reactor or any other type of reactor suitable for conducting metathesis reactions. The metathesis reactor 210 may include a plurality of metathesis reactors in series or in parallel. The metathesis reactor 210 may be operable to contact a butene-containing feed 202 with the composite catalyst of the present disclosure in a metathesis reaction zone 212. The metathesis reactor 210 may include inert packing material 216 upstream and downstream of the metathesis reaction zone 212 to secure the composite catalyst in the metathesis reaction zone 212.

The butene-containing feed 202 may comprise 1-butene, trans-2-butene, cis-2-butene, or combinations of these. The butene-containing feed 202 may further comprise other $C_1$-$C_6$ components. The butene-containing feed 202 may comprise from 10 wt. % to 100 wt. % 1-butene based on the total weight of the butene-containing feed 202. For example, the butene-containing feed 202 may comprise from 10 wt. % to 80 wt. %, from 10 wt. % to 60 wt. %, from 10 wt. % to 40 wt. %, from 10 wt. % to 20 wt. %, from 20 wt. % to 100 wt. %, from 20 wt. % to 80 wt. %, from 20 wt. % to 60 wt. %, from 20 wt. % to 40 wt. %, from 40 wt. % to 100 wt. %, from 40 wt. % to 80 wt. %, from 40 wt. % to 60 wt. %, from 60 wt. % to 100 wt. %, from 60 wt. % to 80 wt. %, or from 80 wt. % to 100 wt. % 1-butene based on the total weight of the butene-containing feed 202. The butene-containing feed 202 may comprise from 10 wt. % to 100 wt. % 2-butene (that is, cis-2-butene, trans-2-butene, or both) based on the total weight of the butene-containing feed 202. For example, the feedstock 140 may comprise from 10 wt. % to 80 wt. %, from 10 wt. % to 60 wt. %, from 10 wt. % to 40 wt. %, from 10 wt. % to 20 wt. %, from 20 wt. % to 100 wt. % to 80 wt. %, from 20 wt. % to 60 wt. %, from 20 wt. % to 40 wt. %, from 40 wt. % to 100 wt. %, from 40 wt. % to 80 wt. %, from 40 wt. % to 60 wt. %, from 60 wt. % to 100 wt. %, from 60 wt. % to 80 wt. %, or from 80 wt. % to 100 wt. % 2-butene based on the total weight of the butene-containing feed 202. Additionally, the butene-containing feed 202 may be substantially free of ethylene. For example, the butene-containing feed 202, which may be substantially free of ethylene, may comprise less than 1 wt. % of ethylene based on the total weight of the butene-containing feed 202.

In one or more embodiments, the butene-containing feed 202 may be a C4 Raffinate stream, such as but not limited to a Raffinate-2 stream. Raffinate is the residue C4 stream from a naphtha cracking process or from a gas cracking process when one or more constituents are removed (the C4 stream typically containing, as its chief components, n-butane, 1-butene, 2-butene, isobutene, and 1,3-butadiene, and optionally some isobutane and said chief components together forming up to 95% or more of the C4 stream). The butene-containing feed 202 may include a raffinate-1 stream. Raffinate-1 is the $C_4$ residual obtained after separation of 1,3-butadiene from the $C_4$ raffinate stream and comprises mainly 2-butene, 1-butene, and isobutene, which may make up from 55 wt. % to 99 wt. % of the raffinate-1 stream. For example, the raffinate-1 stream may comprise from 10 wt. % to 30 wt. % of 2-butene, from 25 wt. % to 50 wt. % of 1-butene, and from 20 wt. % to 50 wt. % isobutene, based on the total weight of the raffinate-1 stream. The butene-containing feed 202 may comprise a raffinate-2 stream. Raffinate-2 is the $C_4$ residual obtained after separation of 1,3-butadiene and isobutene from the $C_4$ raffinate stream and comprise mainly 2-butene, 1-butene, and n-butane, which may make up from 45 wt. % to 99 wt. % of the raffinate-2 stream. For example, the raffinate-2 stream may comprise from 20 wt. % to 60 wt. % of 2-butene, from 10 wt. % to 60 wt. % of 1-butene, and from 15 wt. % to 25 wt. % n-butane, based on the total weight of the raffinate-2 stream. The butene-containing feed 202 may comprise a raffinate-3 stream. Raffinate-3 is the $C_4$ residual obtained after separation of 1,3-butadiene, isobutene, and 1-butene from the $C_4$ raffinate stream and comprises mainly 2-butene, n-butane, and unseparated residual 1-butene, which combined may make up from 40 wt. % to 99 wt. % of the raffinate-3 stream. For example, the raffinate-3 stream may comprise from 30 wt. % to 70 wt. % of 2-butene and from 10 wt. % to 30 wt. % of n-butane, based on the total weight of the raffinate-3 stream. The presence of isobutane, inert gases, and non-olefinic hydrocarbons, such as n-butane, in the butene-containing feed 202 may not negatively affect the target metathesis reactions, but may undergo cracking reactions through contact with the zeolite particles in the composite catalyst.

As depicted in FIG. 1, a butene-containing feed 202 may be introduced into the metathesis reactor 210 and contacted with the composite catalyst in the metathesis reaction zone 212, the composite catalyst may include the ZSM-5 zeolite particles embedded in the mesoporous silica catalyst support material and tungsten oxide as the catalytically active compound dispersed across the outer and pore surfaces of the mesoporous silica catalyst support, the ZSM-5 zeolite particles, or both. Contact of the butene-containing feed 202 with the composite catalyst may cause at least a portion of the butene in the butene-containing feed 202 to react to form propene and other olefins. The reactions may include cross-metathesis, cracking, or both.

The metathesis reaction zone 212 may be maintained at a metathesis reaction temperature sufficient to promote the cross-metathesis reaction of 2-butene and 1-butene. The metathesis reaction temperature may be from 100 degrees Celsius (° C.) to 600° C. For example, the metathesis reaction zone 212 may be maintained at a metathesis reaction temperature of from 100° C. to 550° C., from 100° C. to 450° C., from 100° C. to 400° C., from 100° C. to 300° C., from 100° C. to 250° C., from 100° C. to 150° C., from 150° C. to 600° C., from 150° C. to 550° C., from 150° C. to 450° C., from 150° C. to 400° C., from 150° C. to 300° C., from 150° C. to 250° C., from 250° C. to 600° C., from 250° C. to 550° C., from 250° C. to 450° C., from 250° C. to 400° C., from 250° C. to 300° C., from 300° C. to 600° C., from 300° C. to 550° C., from 300° C. to 450° C., from 300° C. to 400° C., from 400° C. to 600° C., from 400° C. to 550° C., from 400° C. to 450° C., from 450° C. to 600° C., from 450° C. to 550° C., or from 550° C. to 600° C.

The composite catalysts prepared by the spray dry method of the present disclosure may exhibit enhanced metathesis performance compared to conventional metathesis catalysts prepared by conventional techniques, such as wet impregnation or incipient wetness impregnation as well as compared to dual catalyst systems comprising a combination of a metathesis catalyst and a cracking catalyst. The catalytic activity of the spray-dried composite catalyst of the present disclosure was evaluated for conversion of butene to propene in a fixed bed reactor and its performance was compared against a dual catalyst reaction system comprising a conventional metathesis catalyst prepared by wet impregnation and a separate zeolite cracking catalyst. The spray-dried composite catalyst was highly active and stable, and performed comparable to the dual-catalyst system with the conventional metathesis catalyst and the separate cracking catalyst. Thus, the composite catalysts of the present disclosure can provide comparable metathesis performance with a single catalyst that does not require preparation of a catalyst mixture or isolation and separation of two or more reaction zones within the metathesis reactor, which may result in unutilized dead zones within the reactor.

A metathesis effluent 214 comprising the propene and other olefins may be passed out of the metathesis reactor 210. The metathesis effluent 214 may be passed to the metathesis effluent separation system 230 operable to separate the metathesis effluent 214 into a plurality of product streams, such as but not limited to, an ethylene stream 232, a propene stream 234, a C4 stream 236, a C5+ stream 238, or combinations of these. The ethylene stream 232, propene stream 234, or both may be passed to downstream processing units to purify the ethylene, propene, or both. The ethylene, propene, or both may be used as valuable intermediates in the production of polymers and other valuable chemical products. The C4 stream 236 may be recycled back to the metathesis reactor 210 or passed to one or more downstream processing operations. The C5+ stream 238 may be passed to one or more downstream processing operations for further processing.

EXAMPLES

The following examples illustrate one or more additional features of the present disclosure described previously. It should be understood that these examples are not intended to limit the scope of the disclosure or the appended claims in any manner.

Example 1: Preparation of Zeolite—MFI 2000 Cracking Catalyst

In a typical synthesis, 17.04 grams of tetrapropylammonium bromide (TPABr) and 2.96 g ammonium fluoride were dissolved in 300 grams of deionized water and stirred well for 20 minutes to produce a TPABr solution. 48 grams of fumed silica and 0.30 grams of aluminum nitrate were gradually added simultaneously to the TPABr solution while stirring vigorously. Once the solution gelled, the gel was mixed with a spatula for about 10 minutes until homogenized. The obtained gel was placed in a TEFLON®-lined acid digestive bomb and maintained at 200° C. for 2 days. After two days, the digestive bomb was removed from the oven and was quenched in cold water for 30 minutes. The contents of the digestive bomb were filtered and washed with 1 liter of deionized water. The molar composition of gel was 1 $SiO_2$: 0.0005 $Al_2O_3$: 0.08 (TPA)Br: 0.10 $NH_4F$: 20$H_2O$. The solid products obtained were washed with water and dried at 80° C. overnight. The template was removed by calcination in air at 750° C. for 6 hours with a ramp up of 4° C. per minute.

Figure 3:
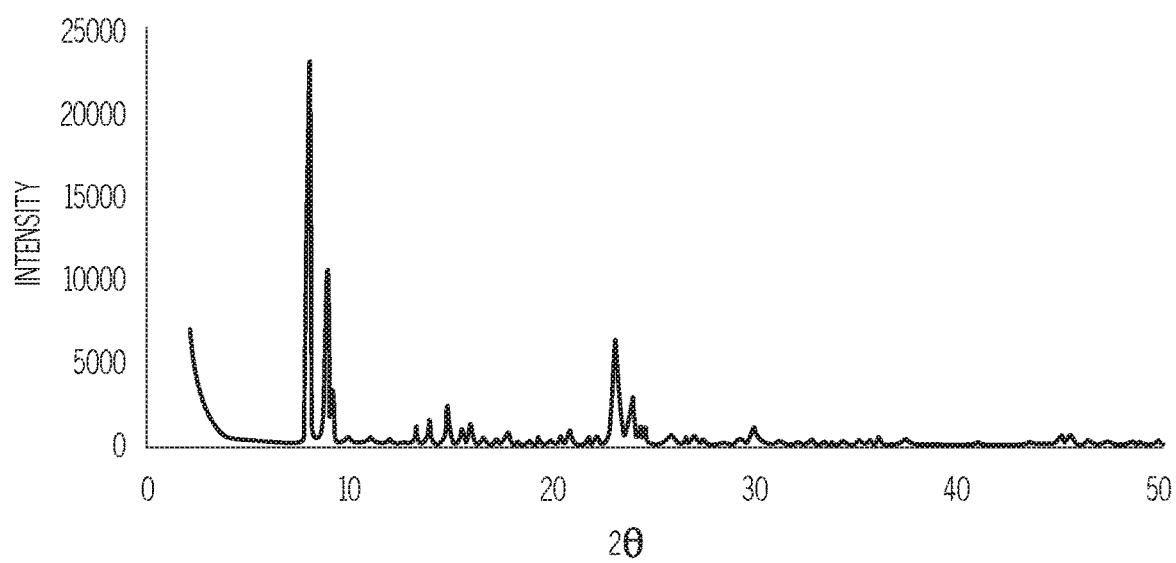
FIG. 3 graphically depicts an X-Ray Diffraction (XRD) profile for a modenite framework inverted (MFI) structured zeolite, according to one or more embodiments shown and described in the present disclosure.

The MFI-2000 cracking catalyst of Example 1 was analyzed using X-Ray Diffraction (XRD). Referring to FIG. 3, the XRD plot for the MFI-2000 cracking catalyst of Example 1 shows the characteristic peaks for the MFI-2000 cracking catalyst at 2-theta equal to 8 degrees)(°, 9°, 23°, and 24°.

Comparative Example 2: Tungsten Oxide on Silica Metathesis Catalyst Prepared by Wet Impregnation In Comparative Example 2, a comparative metathesis catalyst comprising tungsten oxide supported on a mesoporous silica support was prepared. The metathesis catalyst of Comparative Example 2 was prepared through a wet impregnation technique. About 2 grams of the silica support material and about 0.235 g of ammonium metatungstate (99.99% trace metals basis) were added to a round bottom flask. The silica support material was CARiACT® Grade Q-10 mesoporous silica obtained from Fuji Silysia Chemicals, Ltd and calcined at 200° C. for three hours and then at 575° C. for five hours, with a ramping rate of 3° C. per minute. About 20 mL of deionized water was then added to the flask. A magnetic stir bar was added to the flask and the flask is placed on a stir plate that was programmed to run at 500 rpm, for roughly two hours. The magnetic stir bar was removed from the flask, and the flask was connected to a rotary evaporator. The conditions for operations of the rotary evaporator were: rotation set to 171 rpm, temperature of the water bath set to 80° C., vacuum set to 292 millibar, and the cooling liquid (50% water and 50% glycol) was maintained at 6° C. Following that, the catalytic composition was placed in a drying oven overnight at 80° C. The dried catalyst was calcined at 250° C. for 2 hours and at 550° C. for 8 hours, with a ramping rate of 1° C. per minute until the first temperature is reached and 3° C. per minute until the second temperature is reached. Calcination of these samples was carried out in a VULCAN® 3-550 furnace (commercially available from Dentsply Ceramco, headquartered in York, Pa. USA). The comparative metathesis catalyst of Comparative Example 2 included a tungsten oxide loading of 10 weight percent based on the total weight of the comparative metathesis catalyst.

Figure 4:
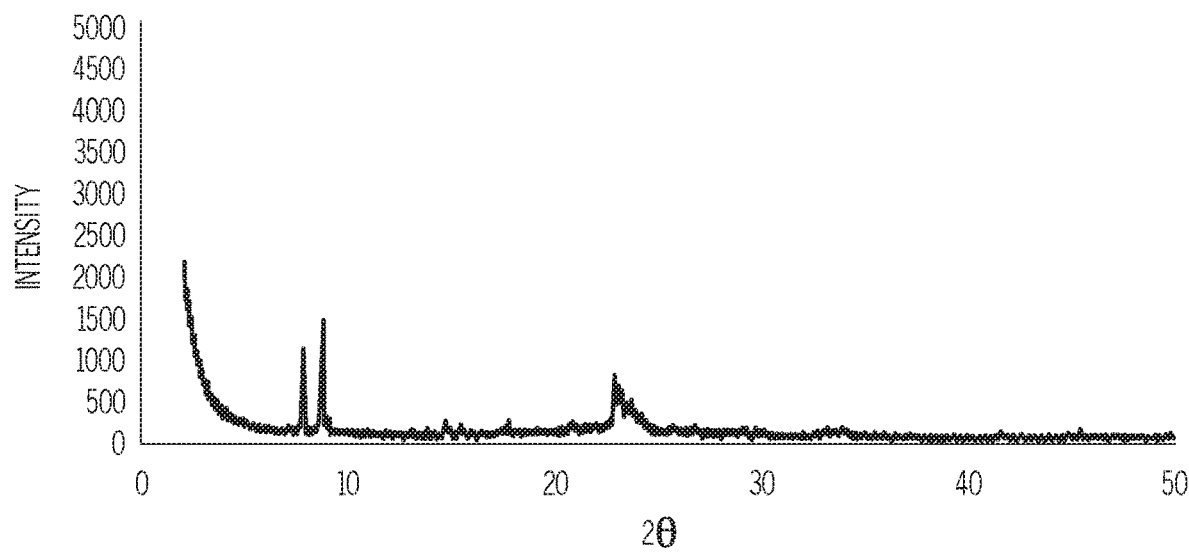
FIG. 4 graphically depicts an XRD profile for a metathesis catalyst of the prior art comprising tungsten oxide supported on a mesoporous silica support.

The metathesis catalyst of Comparative Example 2 was analyzed using X-Ray Diffraction (XRD). The XRD data for the Examples of the present disclosure were collected using a D4 Endeavor X-Ray Diffractometer from Bruker AXS GmbH (Karlsruhe, Germany) and analyzed using DIFFRAC.EVA V4.1.1 version (available from Bruker), which had a built-in PDF library to match the perfect scan. Analyses were carried out at room temperature in the 2-theta range from 20 degrees to 80 degrees. As shown in FIG. 4, the XRD plot for the metathesis catalyst of Comparative Example 2 includes the characteristic peaks for silica as well as characteristic peaks for tungsten oxide in the range of 2-theta of between 20° and 30°.

Additionally, the metathesis catalyst of Comparative Example 2 was subjected to scanning electron microscopy (SEM) to determine the average particle size. The metathesis catalyst of Comparative Example 2 prepared by wet impregnation without spray drying had an average particle size of 81.012 micrometers (μm).

Example 3: Preparation of the Composite Catalyst

In Example 3, a composite catalyst was prepared according to the methods of the present disclosure using the MFI-2000 cracking catalyst of Example 1. A first solution was prepared by combining 33.55 grams of silica, 13 grams of MFI-2000 cracking catalyst from Example 1, and 250 milliliters (mL) of water. The silica was CATiRAC™, grade Q-10 silica from Fuji Silysia Chemicals, Ltd. The mixture of silica and MFI-2000 cracking catalyst in water was stirred for 30 minutes at a speed of greater than 800 rotations per minute (rpm). A second solution comprising 7 grams of surfactant, 35 mL of water, and 70 mL of ethanol was prepared and stirred for 30 minutes at greater than 800 rpm to fully dissolve the surfactant. The surfactant was PLURONIC® P123 poly(ethylene glycol)-block-poly(propylene glycol)-block-poly(ethylene glycol) surfactant obtained from Sigma Aldrich. A third solution was prepared by mixing 4 grams of tungsten precursor (ammonium meta tungstate hexahydrate) with 40 mL of water and shaking the third solution vigorously until all the tungsten precursor was dissolved. The third solution was then combined with the second solution and the resulting mixture was stirred for 10 minutes. The combined mixture of the second solution and third solution was then added to the first solution comprising the silica and MFI-2000 cracking catalyst to produce the spray dryer solution. The spray dryer solution was stirred at a speed of greater than 700 rpm for three days. The resulting spray dryer solution was milky and homogeneous in appearance.

The spray dryer solution was then spray dried using a GEA Niro spray dryer MOBILE MINOR™ for aqueous feeds. The drying chamber of the spray dryer had a cylinder size of 793 millimeters (mm), a height of 660 mm, and a cone angle of 60 degrees. Spray drying was conducted with a target feed flow rate of 240 milliliters per minute (mL/min) although the flow rate was constantly adjusted to maintain the exhaust temperature less than 110° C. The surface temperature of the drying chamber was maintained at 275° C. and the fan speed of the fan withdrawing air and composite catalyst out of the drying chamber was set to 2009 rpm.

To start the spray drying process, the spray dryer was turned on and allowed to gradually heat while feeding deionized water. Once the surface temperature of the drying chamber reached the target temperature of 275° C. and the temperature of the outlet air stabilized, the spray dryer solution was introduced to the spray dryer in place of the deionized water. The composite catalyst was removed from the spray dryer at two locations: the bottom of the cone portion of the drying chamber and a position at the side of the drying chamber just above the conical portion of the drying chamber. The composite catalyst withdrawn from the bottom of the drying chamber will be referred as composite catalyst 3A, and the composite catalyst withdrawn from the side of the drying chamber will be referred to as composite catalyst 3B. The composite catalyst 3B comprised catalyst particles that were lighter in density and slightly smaller in average particle size compared to the composite catalyst 3A.

Figure 5:
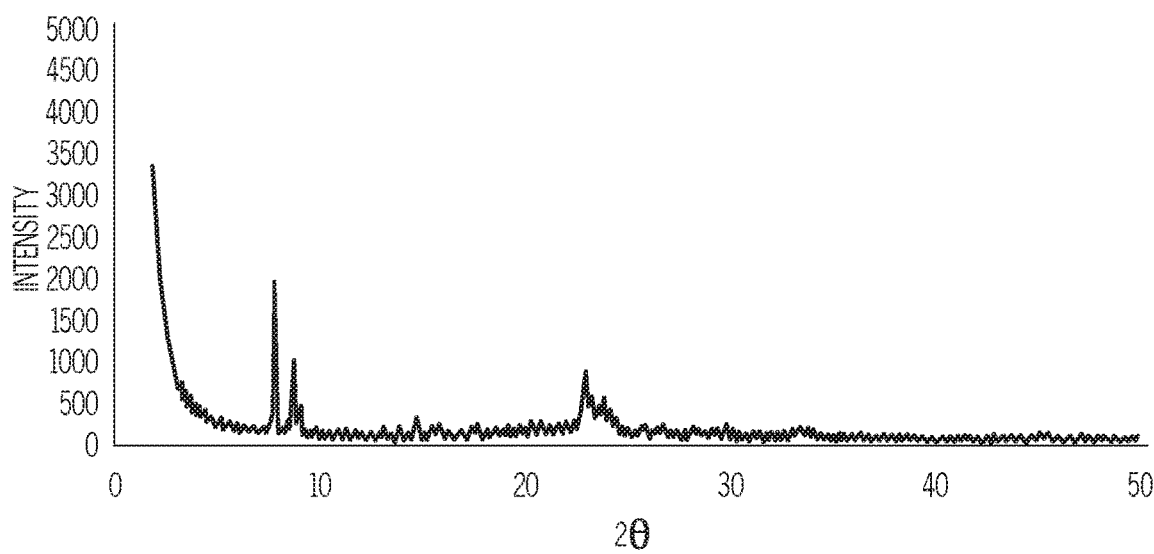
FIG. 5 graphically depicts an XRD profile for a composite catalyst, according to one or more embodiments shown and described in the present disclosure.

The composite catalyst 3A and composite catalyst 3B were calcined according to the calcination process previously described in Example 1. The composite catalyst 3A of Example 3 was analyzed using X-Ray Diffraction (XRD). Referring to FIG. 5, the XRD plot for the composite catalyst 3A of Example 3 includes the characteristic peaks for the MFI-2000 cracking catalyst of Example 1 at 2 theta equal to 8 degrees)(°, 9°, 23°, and 24° as well as the characteristic peak for tungsten oxide at 2 theta equal to about 23.3°.

Additionally, the composite catalyst 3A, composite catalyst 3B, and a 50:50 mixture by weight of composite catalysts 3A and 3B were was subjected to scanning electron microscopy (SEM) to determine the average particle size. The values for the average particle size for the composite catalysts of Example 3 and the metathesis catalyst of Comparative Example 2 are provided in Table 1. As shown in Table 1, the spray drying process in Example 3 produces composite catalysts having average particle sizes that are substantially less than the average particles sizes of conventional metathesis catalysts prepared through wet impregnation, such as those prepared in Comparative Example 2.

TABLE 1

| | Composite Catalyst 3A | Composite Catalyst 3B | Mixture of Composite Catalyst | Metathesis Catalyst of Comp. Ex. 2 |
|---|---|---|---|---|
| Average Particle Size (μm) | 13.332 | 9.866 | 14.212 | 81.012 |

Example 4: Metathesis of Butene Using Composite Catalyst of Example 2

In Example 4, the composite catalyst 3B of Example 3 was used to conduct metathesis of a butene-containing feed. The metathesis reactions were conducted in fixed bed reactor at atmospheric pressure. The fixed bed reactor was a 16-fold High Throughput reactor unit. A fixed amount of 0.2 grams of the composite catalyst 3B was packed into the reactor between two layers of silicon carbide. The silicon carbide was used as an inert packing material to maintain the catalyst in the reactor and did not participate in the metathesis reaction.

The composite catalyst 3B of Example 3 was first pretreated and activated at a temperature of 550° C. under nitrogen at a flow rate of 120 milliliters per minute (mL/min) for 24 hours. The temperature of the fixed bed reactor was adjusted to 500° C. at atmospheric pressure, and a butene-containing feed was introduced to the fixed bed reactor. The butene-containing feed included 10 wt. % isobutane, 20 wt. % n-butane, 12.5 wt. % trans-2-butene, 12.5 wt. % cis-2-butene, and 45 wt. % 1-butene based on the total weight of the butene-containing feed. The butene-containing feed was passed through the fixed bed reactor at a weight hourly space velocity (WHSV) of 7.175 per hour ($h^{-1}$) for 30 hours. Quantitative analysis of the reactor effluent was performed using a gas chromatograph (commercially available as Agilent GC-7890B) with a thermal conductivity detector (TCD) and two flame ionization detectors (FID).

Figure 6:
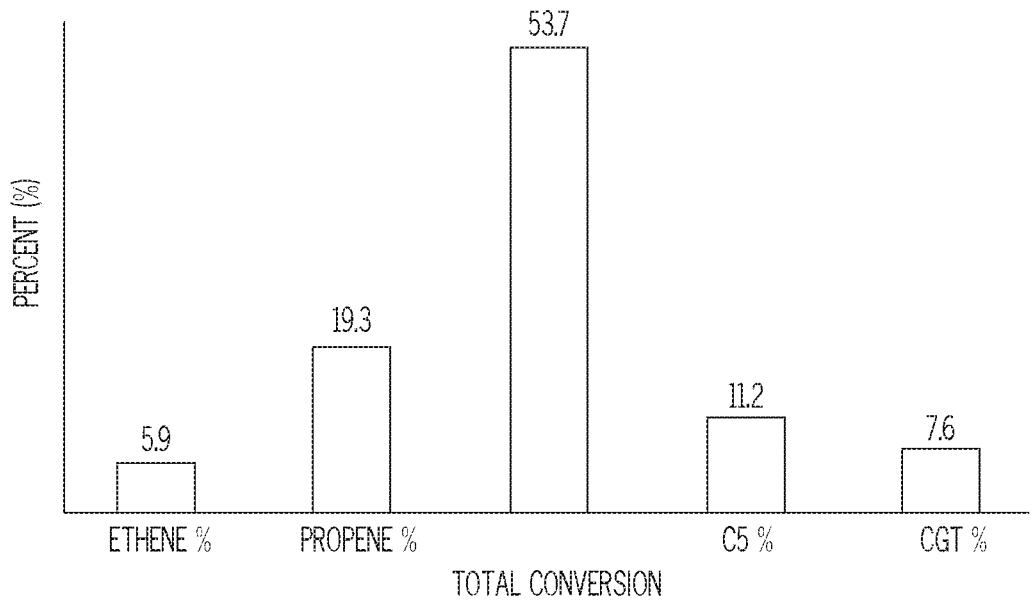
FIG. 6 graphically depicts overall conversion and yield of ethylene, propene, C5 hydrocarbons, and C6+ hydrocarbons from a metathesis reaction conducted with the composite catalyst of FIG. 5, according to one or more embodiments shown and described in the present disclosure.

Referring to FIG. 6, the total conversion of butene and yields of each of ethene, propene, five-carbon hydrocarbons (C5), and hydrocarbons having 6 or more carbons (C6+) are provided as percentages. The conversion and yields in FIG. 6 are the average of 11 samples taken periodically over the 30 hour run time of the experiment. The composite catalyst 3B of Example 3 resulted in a total conversion of 53.7%, a yield of propene of 19.3%, and a yield of ethene of 5.9%.

Comparative Example 5: Metathesis of Butene Using a Dual Catalyst System

In Comparative Example 5, a butene-containing feed was contacted with a dual catalyst system that included the metathesis catalyst of Comparative Example 2 and the MFI-2000 cracking catalyst of Example 1. The metathesis catalyst of Comparative Example 2 (0.1 grams) and the MFI-2000 catalyst of Example 1 (0.1 grams) were packed into the fixed bed reactor with the metathesis catalyst disposed upstream of the MFI-2000 cracking catalyst. The metathesis catalyst of Comparative Example 2 was placed upstream of the MFI-2000 cracking catalyst of Example 1.

The catalysts of the dual catalyst system of Comparative Example 5 were pretreated and activated according to the process described in Example 4. Following pretreatment, the reactor temperature was adjusted to 500° C. at atmospheric pressure, and a butene-containing feed was introduced to the fixed bed reactor. The butene-containing feed was passed through the fixed bed reactor at a weight hourly space velocity (WHSV) of 7.175 per hour ($h^{-1}$) for 30 hours. Quantitative analysis of the reactor effluent was performed using a gas chromatograph (commercially available as Agilent GC-7890B) with a thermal conductivity detector (TCD) and two flame ionization detectors (FID).

Figure 7:
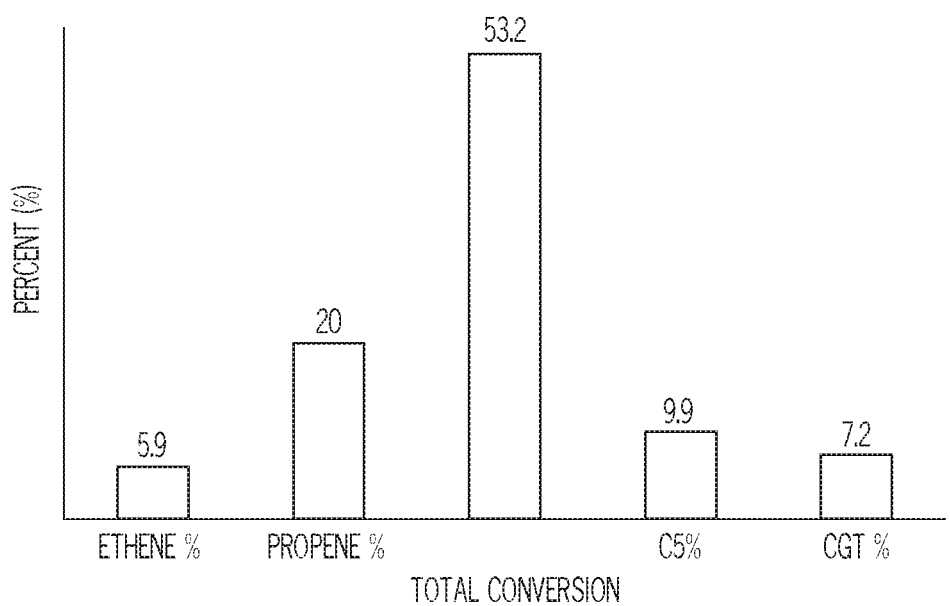
FIG. 7 graphically depicts overall conversion and yield of ethylene, propene, C5 hydrocarbons, and C6+ hydrocarbons from a metathesis reaction conducted with a dual catalyst system comprising the MFI-structured zeolite of FIG. 3 and the metathesis catalyst of the prior art of FIG. 4.

Referring to FIG. 7, the total conversion of butene and yields of each of ethene, propene, five-carbon hydrocarbons (C5), and hydrocarbons having 6 or more carbons (C6+) are provided as percentages. The conversion and yields in FIG. 7 are the average of 11 samples taken periodically over the 30 hour run time of the experiment. The dual catalyst system of Comparative Example 5 resulted in a total conversion of 53.2%, a yield of propene of 20%, and a yield of ethene of 5.9%.

As shown in FIGS. 6 and 7, the composite catalyst of Example 3 (FIG. 6) produced results comparable to the dual catalyst system of Example 5 having the metathesis catalyst of Comparative Example 2 and the zeolite of Example 1 (FIG. 7). In fact, the composite catalyst of Example 3 exhibited a greater overall conversion of butene, which demonstrates overall greater catalytic activity compared to the metathesis catalyst of Comparative Example 2. Not intending to be bound by any particular theory, it is believe that the process for making the composite catalyst of Example 3 according to the present disclosure reduces the average particle size and increases both the surface area and degree of dispersion of the catalytically active compound over the surfaces of the composite catalyst compared to the metathesis catalyst of Comparative Example 2, which was prepared by wet impregnation. This lesser average particle size, greater surface area, and greater dispersion of catalytically active compound on the surfaces are believed to result in greater catalytic activity of the composite catalysts prepared by the methods of the present disclosure compared to metathesis catalysts made using conventional wet impregnation or incipient wetness impregnation synthesis methods.

Example 6: Metathesis of Butene—Influence of Average Particle Size of the Composite Catalyst of Example 3 on Total Conversion and Yield In Example 6, the influence of the average particle size of the composite catalyst of Example 3 on the metathesis of butene was investigated by conducting the metathesis reaction according to the process in Example 4 with the composite catalyst 3A, composite catalyst 3B, and a composite catalyst mixture that included both 3A and 3B. As previously discussed, the average particle size of the composite catalyst 3A was greater than the average particle size of the composite catalyst 3B. The butene metathesis reactions were conducted in accordance with the process described in Example 4 at temperatures of 450° C., 500° C., and 550° C. for each of the composite catalysts and the composite catalyst mixture. The composite catalyst mixture included equal amounts by weight of composite catalyst 3A and composite catalyst 3B. The average yields for propene, ethene, C5 hydrocarbons, and C6+ hydrocarbons resulting for each of the butene metathesis reactions of Example 6 are provided below in Table 2.

TABLE 2

| Yield | Composite Catalyst 3A (heavy) | Composite Catalyst 3B (light) | Composite Catalyst Mixture |
|---|---|---|---|
| Average Particle Size (micrometers) | 13.332 | 9.866 | 14.212 |
| Propene at 450° C. (%) | 21.61 | 20.38 | 21.53 |
| Ethene at 450° C. (%) | 4.97 | 4.93 | 4.96 |
| C5 at 450° C. (%) | 9.95 | 9.56 | 9.77 |
| C6+ at 450° C. (%) | 22.53 | 20.80 | 22.02 |
| Propene at 500° C. (%) | 30.29 | 30.26 | 30.32 |
| Ethene at 500° C. (%) | 8.41 | 8.85 | 8.50 |
| C5 at 500° C. (%) | 8.12 | 7.71 | 7.90 |
| C6+ at 500° C. (%) | 22.25 | 20.28 | 21.63 |
| Propene at 550° C. (%) | 30.02 | 32.17 | 31.45 |
| Ethene at 550° C. (%) | 9.45 | 11.15 | 10.29 |
| C5 at 550° C. (%) | 6.73 | 5.73 | 6.22 |
| C6+ at 550° C. (%) | 19.67 | 17.30 | 18.83 |

As shown by the results in Table 2, the composite catalyst 3B having the smaller average particle size produced better selectivity towards propene at greater metathesis temperatures compared to the composite catalyst 3A having the greater average particle size. At lower temperatures, the composite catalyst 3A provided better metathesis performance with respect to propene selectivity.

Calculation Methodologies

Determination of "Conversion" was calculated according to formula 1.

$$\text{Conversion} = 100 - (\text{CisButene Yield} + \text{TransButene Yield}) \quad (1)$$

Similarly, determination of "Conversion-$C_4$" was calculated according to formula 2.

$$\text{Conversion-C4} = 100 - (\text{CisButene Yield} + \text{TransButene Yield} + \text{IsoButene Yield} + \text{1-Butene Yield}) \quad (2)$$

Determination of "Selectivity" was calculated according to formula 3.

$$\text{Selectivity} = \frac{\text{Yield of Product}}{\text{Conversion}} \times 100 \quad (3)$$

A first aspect of the present disclosure is directed to a method of preparing a composite catalyst. The method may include combining a catalyst support material, zeolite particles, a triblock copolymer surfactant, a catalytically active compound precursor, and a diluent to produce a catalyst precursor composition. The method may further include mixing the catalyst precursor composition to produce a catalyst precursor mixture in which the catalyst support material and the zeolite particles are suspended in the diluent and spray drying the catalyst precursor mixture. The spray drying may include atomizing the catalyst precursor mixture to produce a plurality of droplets and drying the plurality of droplets in a drying chamber. Drying may remove the diluent from each of the plurality of droplets to form agglomerates comprising the zeolite particles at least partially secured within the catalyst support material. Drying may also cause the catalytically active compound precursor to react to form a catalytically active compound deposited on outer surfaces and pore surfaces of the catalyst support material, the zeolite particles, or both.

A second aspect of the present disclosure may include the first aspect, in which the catalyst support material may comprise solid particles comprising at least one of silica, fumed silica, alumina, fumed alumina, titania, fumed titania, or combinations of these.

A third aspect of the present disclosure may include either one of the first or second aspects, in which the catalyst support material may comprise mesoporous silica.

A fourth aspect of the present disclosure may include any one of the first through third aspects, in which the catalyst support material may comprise a preformed catalyst support material.

A fifth aspect of the present disclosure may include any one of the first through fourth aspects, in which the method may not include synthesizing the catalyst support material from one or more precursors.

A sixth aspect of the present disclosure may include any one of the first through fifth aspects, in which the catalyst support material may have an average pore diameter of from 2.5 nanometers to 40 nanometers.

A seventh aspect of the present disclosure may include any one of the first through sixth aspects, in which the catalyst support material may have a total pore volume of at least 0.600 milliliters per gram.

An eighth aspect of the present disclosure may include any one of the first through seventh aspects, in which the catalyst support material may have a surface area of from 250 meters squared per gram to 600 meters squared per gram.

A ninth aspect of the present disclosure may include any one of the first through eighth aspects, in which the zeolite particles may comprise a mordenite framework inverted structured zeolite.

A tenth aspect of the present disclosure may include any one of the first through ninth aspects, in which the zeolite particles may comprise ZSM-5 zeolite.

An eleventh aspect of the present disclosure may include any one of the first through tenth aspects, in which the zeolite particles may comprise silica and alumina and a weight ratio of silica to alumina is from 10:1 to 6000:1.

A twelfth aspect of the present disclosure may include any one of the first through eleventh aspects, in which the zeolite particles may have an average particle size of from 5 micrometers to 35 micrometers.

A thirteenth aspect of the present disclosure may include any one of the first through twelfth aspects, in which the triblock copolymer surfactant may be poly(ethylene glycol)-block-poly(propylene glycol)-block-poly(ethylene glycol).

A fourteenth aspect of the present disclosure may include any one of the first through thirteenth aspects, comprising mixing the catalyst precursor mixture for a period of time sufficient to produce a stable catalyst precursor mixture.

A fifteenth aspect of the present disclosure may include any one of the first through fourteenth aspects, comprising mixing the catalyst precursor composition for a time of greater than or equal to 72 hours.

A sixteenth aspect of the present disclosure may include any one of the first through fifteenth aspects, in which the combining may comprise preparing a first mixture, a second mixture, and a third mixture. The first mixture may include the catalyst support material, the zeolite particles, and a first portion of the diluent. The second mixture may include the triblock copolymer surfactant and a second portion of the diluent. The third mixture may include the catalytically active compound precursor and a third portion of the diluent.

A seventeenth aspect of the present disclosure may include the sixteenth aspect, in which the combining may further comprise combining the second mixture and the third mixture to produce a fourth mixture and combining the first mixture and the fourth mixture to produce the catalyst precursor composition.

An eighteenth aspect of the present disclosure may include any one of the first through seventeenth aspects, in which the catalyst precursor mixture may further comprise an alcohol.

A nineteenth aspect of the present disclosure may include any one of the first through eighteenth aspects, in which the drying chamber is maintained at a temperature of from 200° C. to 300° C.

A twentieth aspect of the present disclosure may include the nineteenth aspect, further comprising removing a first composite catalyst from the drying chamber at a first outlet disposed at a bottom of the drying chamber and removing a second composite catalyst from the drying chamber at a second outlet upstream of the first outlet.

A twenty-first aspect of the present disclosure may include the twentieth aspect, where the second composite catalyst may have an average particle size less than an average particle size of the first composite catalyst.

A twenty-second aspect of the present disclosure may include either of the twentieth or twenty-first aspects, where the second composite catalyst may have a density less than a density of the first composite catalyst.

A twenty-third aspect of the present disclosure may include any one of the first through twenty-second aspects, further comprising calcining the composite catalyst at a temperature of from 200° C. to 700° C.

A twenty-fourth aspect of the present disclosure may include any one of the first through twenty-third aspects, in which the catalytically active compound precursor may comprise a metal selected from molybdenum, rhenium, tungsten, manganese, titanium, cerium, or any combination of these.

A twenty-fifth aspect of the present disclosure may include any one of the first through twenty-fourth aspects, in which the catalytically active compound precursor may comprise tungsten.

A twenty-sixth aspect of the present disclosure may include any one of the first through twenty-fifth aspects, in which the catalytically active compound precursor may comprise ammonium metatungstate hydrate.

A twenty-seventh aspect of the present disclosure may include any one of the first through twenty-fourth aspects, in which the catalytically active compound may comprise an oxide of a metal selected from molybdenum, rhenium, tungsten, manganese, titanium, cerium, or any combination of these.

A twenty-eighth aspect of the present disclosure may include any one of the first through twenty-seventh aspects, in which the catalytically active compound may comprise tungsten oxide.

A twenty-ninth aspect of the present disclosure may include any one of the first through twenty-eighth aspects, in which the catalyst precursor mixture may comprise from 5 weight percent to 50 weight percent zeolite particles based on the dry weight of the catalyst precursor mixture.

A thirtieth aspect of the present disclosure may include any one of the first through twenty-ninth aspects, in which the catalyst precursor mixture may comprise from 20 weight percent to 90 weight percent catalyst support material based on the dry weight of the catalyst precursor mixture.

A thirty-first aspect of the present disclosure may include any one of the first through thirtieth aspects, in which the catalyst precursor mixture may comprise from 0.1 weight percent to 25 weight percent catalytically active compound precursor based on the dry weight of the catalyst precursor mixture.

A thirty-third aspect of the present disclosure may include any one of the first through thirty-second aspects, in which the catalyst precursor mixture may comprise from 1 weight percent to 20 weight percent triblock copolymer surfactant based on the dry weight of the catalyst precursor mixture.

A thirty-fourth aspect of the present disclosure may include any one of the first through thirty-third aspects, in which the catalyst precursor mixture may comprise from 50 weight percent to 95 weight percent diluent based on the total weight of the catalyst precursor mixture.

A thirty-fifth aspect of the present disclosure may include any one of the first through thirty-fourth aspects, in which the catalyst precursor mixture may comprise from 1 weight percent to 50 weight percent solids.

A thirty-sixth aspect of the present disclosure may include any one of the first through thirty-fifth aspects and may be directed to a catalyst prepared by the method of any one of the first through thirty-fifth aspects.

A thirty-seventh aspect of the present disclosure may include any one of the first through thirty-sixth aspects, where the composite catalyst may have an average particle size of from 1 micrometer to 80 micrometers.

A thirty-eighth aspect of the present disclosure may include any one of the first through thirty-seventh aspects, where the composite catalyst may comprise from 5 weight percent to 50 weight percent zeolite particles based on the total weight of the composite catalyst.

A thirty-ninth aspect of the present disclosure may include any one of the first through thirty-eighth aspects, where the composite catalyst may comprise from 20 weight percent to 90 weight percent catalyst support material based on the total weight of the composite catalyst.

A fortieth aspect of the present disclosure may include any one of the first through thirty-ninth aspects, where the composite catalyst may comprise from 0.1 weight percent to 25 weight percent catalytically active compound based on the total weight of the composite catalyst.

A forty-first aspect of the present disclosure may include any one of the first through fortieth aspects and may be directed to a process for producing propene. The method may include contacting a butene-containing feed with the composite catalyst at a reaction temperature, where the composite catalyst may be prepared by any of the methods of the first through fortieth aspects. The contacting may cause at least a portion of the butene to undergo chemical reaction to produce a reaction effluent comprising at least propene. The method may further include separating at least a portion of the propene from the reactor effluent.

A forty-second aspect of the present disclosure may be directed to a method for producing propene. The method may include contacting a butene-containing feed with a composite catalyst at a reaction temperature. The contacting may cause at least a portion of the butene to undergo chemical reaction to produce a reaction effluent comprising at least propene. The composite catalyst may be prepared by a method that may include combining a catalyst support material, zeolite particles, a triblock copolymer surfactant, a catalytically active compound precursor, and a diluent to produce a catalyst precursor composition. The method for producing the composite catalyst may further include mixing the catalyst precursor composition to produce a catalyst precursor mixture in which the catalyst support material and the zeolite particles are suspended in the diluent and spray drying the catalyst precursor mixture. The spray drying may include atomizing the catalyst precursor mixture to produce a plurality of droplets and drying the plurality of droplets in a drying chamber. Drying may remove the diluent from each of the plurality of droplets to form agglomerates comprising the zeolite particles at least partially secured within the catalyst support material. Drying may also cause the catalytically active compound precursor to react to form a catalytically active compound deposited on outer surfaces and pore surfaces of the catalyst support material, the zeolite particles, or both. The method for producing propene may further include separating at least a portion of the propene from the reactor effluent.

A forty-third aspect of the present disclosure may include any one of the forty-first through forty-second aspects, where the butene-containing feed may comprise 1-butene, trans-2 butene, cis-2-butene, or combinations of these.

A forty-fourth aspect of the present disclosure may include any one of the forty-first through forty-third aspects, in which the butene-containing feed may be substantially free of ethylene, such as comprising less than 1 weight percent ethylene.

A forty-fifth aspect of the present disclosure may include any one of the forty-first through forty-fourth aspects, where the butene-containing feed may comprise a raffinate-2 stream, a raffinate-3 stream, or combinations of these.

A forty-sixth aspect of the present disclosure may include any one of the forty-first through forty-fifth aspects, in which the reaction temperature may be from 400° C. to 600° C.

A forty-seventh aspect of the present disclosure may include any one of the forty-first through forty-sixth aspects, further comprising contacting the butene-containing feed with an isomerization catalyst to produce an isomerization effluent and contacting the isomerization effluent with the composite catalyst to produce the reaction effluent comprising propene.

A forty-eighth aspect of the present disclosure may include any one of the forty-first through forty-seventh aspects, comprising separating the reaction effluent into a plurality of product streams.

A forty-ninth aspect of the present disclosure may include the forty-eighth aspect, where the product streams may include at least one of an ethylene stream, a propene stream, a C4 stream, a C5+ stream, or combinations of these.

It is noted that one or more of the following claims utilize the term "where" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constitutent, for example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the appended claims should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A method of preparing a composite catalyst for use in isomerization, metathesis, and cracking reactions, the method comprising:
   combining a catalyst support material, zeolite particles, a triblock copolymer surfactant, a catalytically active compound precursor, and a diluent to produce a catalyst precursor composition;
   mixing the catalyst precursor composition to produce a catalyst precursor mixture in which the catalyst support material and the zeolite particles are suspended in the diluent; and
   spray drying the catalyst precursor mixture, where spray drying comprises:
      atomizing the catalyst precursor mixture to produce a plurality of droplets; and
      drying the plurality of droplets in a drying chamber, where drying removes the diluent from each of the plurality of droplets to form agglomerates comprising the zeolite particles at least partially secured within the catalyst support material and causes the catalytically active compound precursor to react to form a catalytically active compound deposited on outer surfaces and pore surfaces of the catalyst support material, the zeolite particles, or both.

2. The method of claim 1 in which the catalyst support material comprises solid particles comprising at least one of silica, fumed silica, alumina, fumed alumina, titania, fumed titania, or combinations of these.

3. The method of claim 1 in which the zeolite particles comprise a mordenite framework inverted structured zeolite.

4. The method of claim 1 where the zeolite particles comprise ZSM-5 zeolite.

5. The method of claim 1, in which the zeolite particles have an average particle size of from 5 micrometers to 35 micrometers.

6. The method of claim 1 in which the triblock copolymer surfactant is poly(ethylene glycol)-block-poly(propylene glycol)-block-poly(ethylene glycol).

7. The method of claim 1 comprising mixing the catalyst precursor composition for a period of time sufficient to produce a stable catalyst precursor mixture.

8. The method of claim 1 in which the combining comprises preparing a first mixture, a second mixture, and a third mixture, where:
the first mixture comprises:
the catalyst support material;
the zeolite particles; and
a first portion of the diluent;
the second mixture comprises:
the triblock copolymer surfactant; and
a second portion of the diluent; and
the third mixture comprises:
the catalytically active compound precursor; and
a third portion of the diluent.

9. The method of claim 8 in which the combining further comprises:
combining the second mixture and the third mixture to produce a fourth mixture, and
combining the first mixture and the fourth mixture to produce the catalyst precursor composition.

10. The method of claim 1 in which the drying chamber is maintained at a temperature of from 200° C. to 300° C.

11. The method of claim 1 further comprising:
removing a first composite catalyst from the drying chamber at a first outlet disposed at a bottom of the drying chamber; and
removing a second composite catalyst from the drying chamber at a second outlet upstream of the first outlet, where the second composite catalyst has an average particle size or a density less than an average particle size or a density, respectively of the first composite catalyst.

12. The method of claim 1 in which the catalytically active compound precursor comprises a metal selected from molybdenum, rhenium, tungsten, manganese, titanium, cerium, or any combination of these.

13. The method of claim 1 in which the catalytically active compound precursor comprises tungsten.

14. The method of claim 1 in which the catalytically active compound comprises an oxide of a metal selected from molybdenum, rhenium, tungsten, manganese, titanium, cerium, or any combination of these.

15. The method of claim 1 in which the catalyst precursor mixture comprises from 5 weight percent to 50 weight percent zeolite particles based on the dry weight of the catalyst precursor mixture.

* * * * *